(12) United States Patent
Kagan et al.

(10) Patent No.: US 11,543,306 B2
(45) Date of Patent: Jan. 3, 2023

(54) ULTRA-SENSITIVE, MECHANICALLY-RESPONSIVE OPTICAL METASURFACES VIA STRAIN AMPLIFICATION

(71) Applicant: The Trustees of The University of Pennsylvania, Philadelphia, PA (US)

(72) Inventors: Cherie R. Kagan, Bala Cynwyd, PA (US); Kevin Turner, Wayne, PA (US); Wenxiang Chen, Urbana, IL (US); Yijie Jiang, Corinth, TX (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 196 days.

(21) Appl. No.: 17/026,468

(22) Filed: Sep. 21, 2020

(65) Prior Publication Data
US 2021/0088392 A1  Mar. 25, 2021

Related U.S. Application Data

(60) Provisional application No. 62/904,784, filed on Sep. 24, 2019.

(51) Int. Cl.
| | | |
|---|---|---|
| *G01L 1/00* | (2006.01) | |
| *G01L 1/18* | (2006.01) | |
| *A61B 5/00* | (2006.01) | |
| *G01L 1/22* | (2006.01) | |

(52) U.S. Cl.
CPC ............... *G01L 1/18* (2013.01); *A61B 5/441* (2013.01); *G01L 1/2287* (2013.01); *A61B 2562/0261* (2013.01)

(58) Field of Classification Search
CPC ........ B25J 9/163; E21B 19/165; E21B 44/00; G01L 5/00; G01N 19/08
See application file for complete search history.

(56) References Cited

U.S. PATENT DOCUMENTS

| | | | |
|---|---|---|---|
| 10,715,078 B2 * | 7/2020 | Jeon | F16M 11/38 |
| 2019/0006165 A1 * | 1/2019 | Corr | H01J 49/165 |
| 2020/0408663 A1 * | 12/2020 | Imai | G01N 15/1434 |
| 2022/0247694 A1 * | 8/2022 | Jackson | G06F 9/5077 |

OTHER PUBLICATIONS

Abaqus Theory Manual, v. 6.9; Dassault Systemes Simulia Corp.: Providence, 2009. http://130.149.89.49:2080/v6.9/books/stm/default.htm.
Aieta et al., "Aberration-Free Ultrathin Flat Lenses and Axicons at Telecom Wavelengths Based on Plasmonic Metasurfaces," Nano. Lett., 2012, vol. 12, pp. 4932-4936.

(Continued)

*Primary Examiner* — Max H Noori
*Assistant Examiner* — Masoud H Noori
(74) *Attorney, Agent, or Firm* — BakerHostetler

(57) ABSTRACT

Provided are structurally-reconfigurable, optical metasurfaces constructed by, for example, integrating a plasmonic lattice array in the gap between a pair of microbodies that serve to locally amplify the strain created on an elastomeric substrate by an external mechanical stimulus. The spatial arrangement and therefore the optical response of the plasmonic lattice array is reversible.

27 Claims, 22 Drawing Sheets
(22 of 22 Drawing Sheet(s) Filed in Color)

(56) References Cited

OTHER PUBLICATIONS

Aksu et al., "Flexible Plasmonics on Unconventional and Nonplanar Substrates," Adv. Mater., 2011, vol. 23, pp. 4422-4430.
Amjadi et al., "Stretchable, Skin-Mountable, and Wearable Strain Sensors and Their Potential Applications: A Review," Adv. Funct. Mater., 2016, vol. 26, pp. 1678-1698.
Arbabi et al., "MEMS-Tunable Dielectric Metasurface Lens," Nat. Commun., 2018, vol. 9, 812.
Caglayan et al., "Near-Infrared Metatronic Nanocircuits by Design," Phys. Rev. Lett., 2013, vol. 111, 073904.
Chen et al., "Large-Area Nanoimprinted Colloidal Au Nanocrystal-Based Nanoantennas for Ultrathin Polarizing Plasmonic Metasurfaces," Nano. Lett., 2015, vol. 15, pp. 5254-5260.
Chen et al., "Ultra-Sensitive, Mechanically-Responsive Optical Metasurfaces via Strain Amplification," ACS Nano., 2018, 36 pages.
Chena et al., "Supporting Information for Ultra-sensitive, mechanically-responsive optical metasurfaces via strain amplification," 2018, 26 pages.
Chu et al., "Active Dielectric Metasurface Based on Phase-Change Medium," Laser Photon. Rev., 2016, vol. 10, pp. 986-994.
Ee et al., "Tunable Metasurface and Flat Optical Zoom Lens on a Stretchable Substrate," Nano. Lett., 2016, vol. 16, pp. 2818-2823.
Ellenbogen et al., "Chromatic Plasmonic Polarizers for Active Visible Color Filtering and Polarimetry," Nano. Lett., 2012, vol. 12, pp. 1026-1031.
Falcone et al., "Babinet Principle Applied to the Design of Metasurfaces and Metamaterials," Phys. Rev. Lett., 2004, vol. 93, 197401.
Gao et al., "Optics and Nonlinear Buckling Mechanics in Large-Area, Highly Stretchable Arrays of Plasmonic Nanostructures," ACS Nano., 2015, vol. 9, pp. 5968-5975.
Greybush et al., "Plasmon Resonances in Self-Assembled Two-Dimensional Au Nanocrystal Metamolecules," ACS Nano., 2017, vol. 11, pp. 2917-2927.
Gutruf et al., "Mechanically Tunable Dielectric Resonator Metasurfaces at Visible Frequencies," ACS Nano., 2016, vol. 10, pp. 133-141.
Hao et al., "Symmetry Breaking in Plasmonic Nanocavities: Subradiant LSPR Sensing and a Tunable Fano Resonance," Nano. Lett., 2008, vol. 8, pp. 3983-3988.
Hu, "Film-edge-induced Stress in Substrates," J. Appl. Phys., 1979, vol. 50, pp. 4661-4666.
Huang et al., "Gate-Tunable Conducting Oxide Metasurfaces," Nano Lett., 2016, vol. 16, pp. 5319-5325.
Kamali et al., "Highly Tunable Elastic Dielectric Metasurface Lenses," Laser Photon. Rev., 2016, vol. 10, pp. 1002-1008.
Kang et al., "Ultrasensitive Mechanical Crack-Based Sensor Inspired by the Spider Sensory System," Nature, 2014, vol. 516, pp. 222-226.
Khorasaninejad et al., "Achromatic Metasurface Lens at Telecommunication Wavelengths," Nano. Lett., 2015, vol. 15, pp. 5358-5362.
Khorasaninejad et al., "Metalenses: Versatile Multifunctional Photonic Components," Science, 2017, vol. 358, 1146.
Kravets et al., "Extremely Narrow Plasmon Resonances Based on Diffraction Coupling of Localized Plasmons in Arrays of Metallic Nanoparticles," Phys. Rev. Lett., 2008, vol. 101, 087403.
Kristensen et al., "Plasmonic Colour Generation," Nat. Rev. Mater., 2016, vol. 2, 16088.
Kumar et al., "Printing Colour at the Optical Diffraction Limit," Nat. Nanotechnol., 2012, vol. 7, pp. 557-561.
Lacour et al., "Stretchable Interconnects for Elastic Electronic Surfaces," Proc. IEEE, 2005, vol. 93, pp. 1459-1467.
Lapine et al., "Structural Tunability in Metamaterials," Appl. Phys. Lett., 2009, vol. 95, 084105.
Li et al., "A Highly Stretchable Autonomous Self-Healing Elastomer," Nat. Chem., 2016, vol. 8, pp. 618-624.
Liberal et al., "Near-Zero Refractive Index Photonics," Nat. Photonics, 2017, vol. 11, pp. 149-158.
Liu et al., "Out-of-Plane Designed Soft Metasurface for Tunable Surface Plasmon Polariton," Nano. Lett., 2018, vol. 18, pp. 1435-1441.
Liu et al., "Strong Exciton-Plasmon Coupling in MoS2 Coupled with Plasmonic Lattice," Nano Lett., 2016, vol. 16, pp. 1262-1269.
Lu et al., "Highly Sensitive Skin-Mountable Strain Gauges Based Entirely on Elastomers," Adv. Funct. Mater., 2012, vol. 22, pp. 4044-4050.
Luk'yanchuk et al., "The Fano Resonance in Plasmonic Nanostructures and Metamaterials," Nat. Mater., 2010, vol. 9, pp. 707-715.
Malek et al., "Strain Multiplexed Metasurface Holograms on a Stretchable Substrate," Nano. Lett., 2017, vol. 17, pp. 3641-3645.
Ni et al., "Metasurface Holograms for Visible Light," Nat. Commun., 2013, vol. 4, 2807.
Olson et al., "Vivid, Full-Color Aluminum Plasmonic Pixels," Proc. Natl. Acad. Sci., 2014, vol. 111, pp. 14348-14353.
Ou et al., "An Electromechanically Reconfigurable Plasmonic Metamaterial Operating in the near-Infrared," Nat. Nanotechnol., 2013, vol. 8, pp. 252-255.
Polavarapu et al., "Towards Low-Cost Flexible Substrates for Nanoplasmonic Sensing," Phys. Chem. Chem. Phys., 2013, vol. 15, 5288.
Pryce et al., "Highly Strained Compliant Optical Metamaterials with Large Frequency Tunability," Nano Lett., 2010, vol. 10, pp. 4222-4227.
Rayleigh et al., "On the Dynamical Theory of Gratings," Proc. R. Soc. A, 1907, vol. 79, pp. 399-416.
Rogel et al., "Spontaneous Buckling of Multiaxially Flexible and Stretchable Interconnects Using PDMS/Fibrous Composite Substrates," Adv. Mater. Interfaces, 2017, vol. 4, 1600946.
Shalaev et al., "Optical Negative-Index Metamaterials," Nat. Photonics., 2007, vol. 1, pp. 41-48.
She et al., "Adaptive Metalenses with Simultaneous Electrical Control of Focal Length, Astigmatism, and Shift," Sci. Adv., 2018, vol. 4, eaap9957.
Smith et al., "Metamaterials and Negative Refractive Index," Science, 2004, pp. 305, pp. 788-792.
Tao et al., "Reconfigurable Terahertz Metamaterials," Phys. Rev. Lett., 2009, vol. 103, 147401.
Tseng et al., "Two-Dimensional Active Tuning of an Aluminum Plasmonic Array for Full-Spectrum Response," Nano. Lett., 2017, vol. 17, pp. 6034-6039.
Wang et al., "Nanosphere Arrays with Controlled Sub-10-Nm Gaps as Surface-Enhanced Raman Spectroscopy Substrates," J. Am. Chem. Soc., 2005, vol. 127, pp. 14992-14993.
Yamada et al., "A Stretchable Carbon Nanotube Strain Sensor for Human-Motion Detection," Nat. Nanotechnol., 2011, vol. 6, pp. 296-301.
Yang et al., "Programmable and Reversible Plasmon Mode Engineering," Proc. Natl. Acad. Sci., 2016, vol. 113, pp. 14201-14206.
Ye et al., "High-Performance Plasmonic Sensors Based on Two-Dimensional Ag Nanowell Crystals," Adv. Opt. Mater., 2014, vol. 2, pp. 779-787.
Yoo et al., "Template-Stripped Tunable Plasmonic Devices on Stretchable and Rollable Substrates," ACS Nano., 2015, vol. 9, pp. 10647-10654.
Yu et al., "Flat Optics with Designer Metasurfaces," Nat. Mater., 2014, vol. 13, pp. 139-150.
Zhang et al., "Fabrication of Gold-Coated PDMS Surfaces with Arrayed Triangular Micro/nanopyramids for Use as SERS Substrates," Beilstein J. Nanotechnol., 2017, vol. 8, pp. 2271-2282.
Zhao et al., "Twisted Optical Metamaterials for Planarized Ultrathin Broadband Circular Polarizers," Nat. Commun., 2012, vol. 3, 870.
Zheludev et al., "From Metamaterials to Metadevices," Nat. Mater., 2012, vol. 11, pp. 917-924.
Zheludev et al., "Reconfigurable Nanomechanical Photonic Metamaterials," Nat. Nanotechnol., 2016, vol. 11, pp. 16-22.
Zheng et al., "Metasurface Holograms Reaching 80% Efficiency," Nat. Nanotechnol., 2015, vol. 10, pp. 308-312.
Zhou et al., "Lasing Action in Strongly Coupled Plasmonic Nanocavity Arrays," Nat. Nanotechnol., 2013, vol. 8, pp. 506-511.

(56) References Cited

OTHER PUBLICATIONS

Zhou et al., "Tunable Subradiant Lattice Plasmons by out-of-Plane Dipolar Interactions," Nat. Nanotechnol., 2011, vol. 6, pp. 423-427.

* cited by examiner

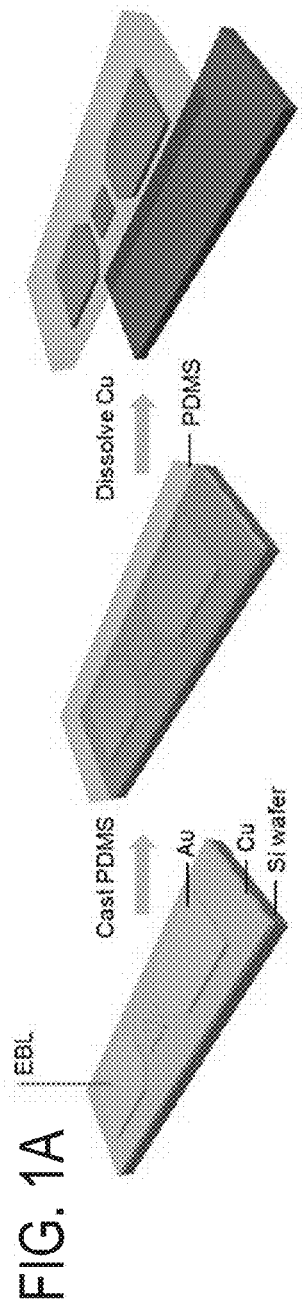
FIG. 1A
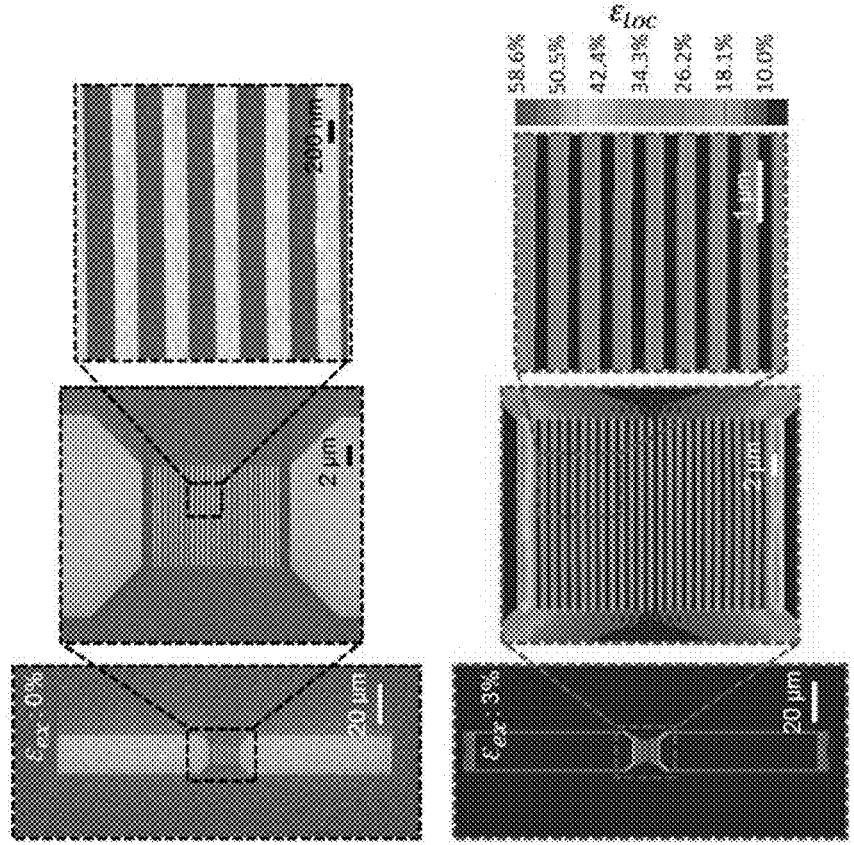
FIG. 1C
FIG. 1D
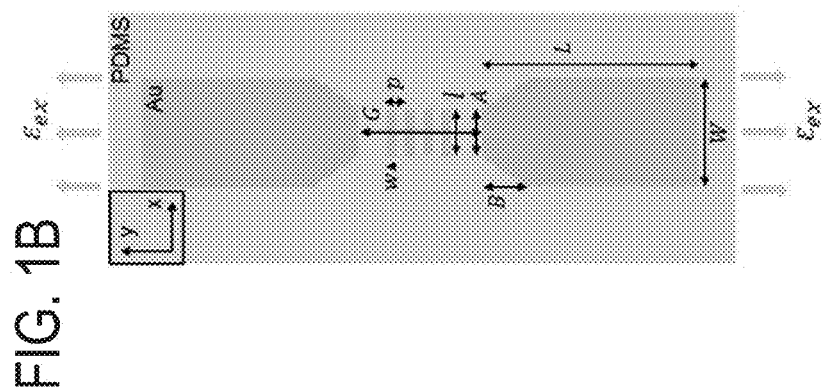
FIG. 1B

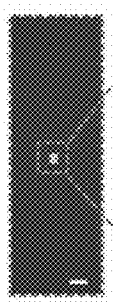 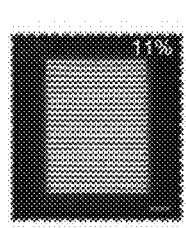  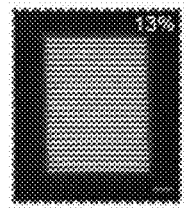
FIG. 2A　　FIG. 2B　　FIG. 2C　　FIG. 2D
 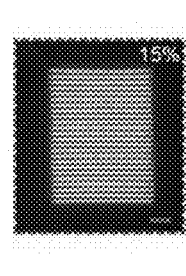 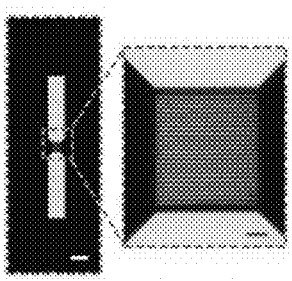 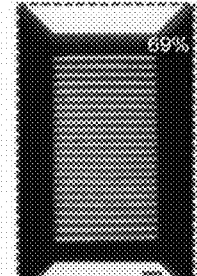
FIG. 2E　　FIG. 2F　　FIG. 2G　　FIG. 2H
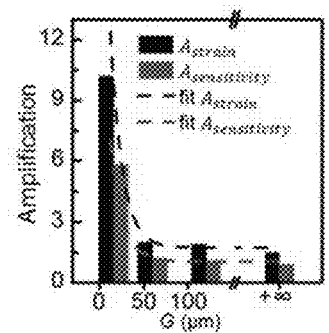
FIG. 2I

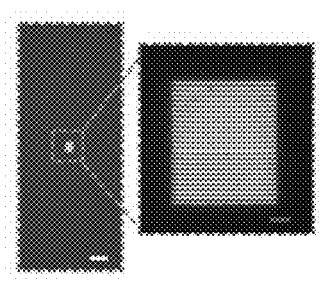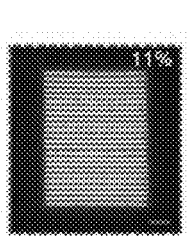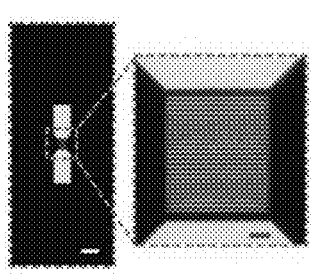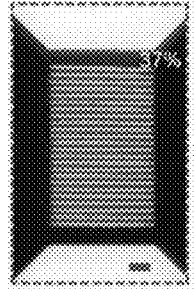
FIG. 3A    FIG. 3B    FIG. 3C    FIG. 3D
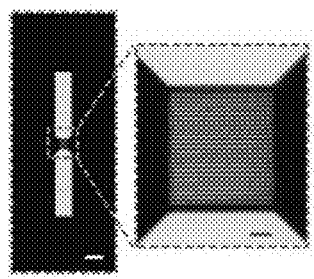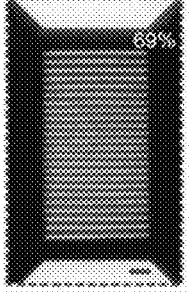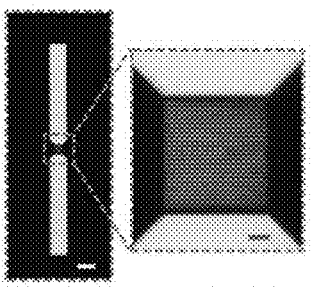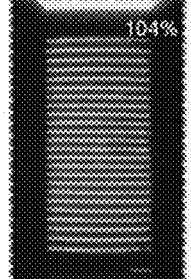
FIG. 3E    FIG. 3F    FIG. 3G    FIG. 3H
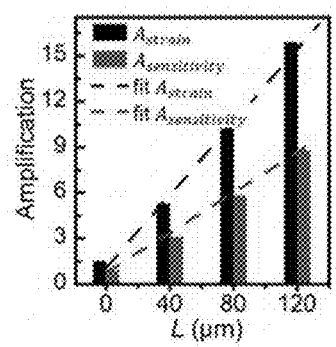
FIG. 3I

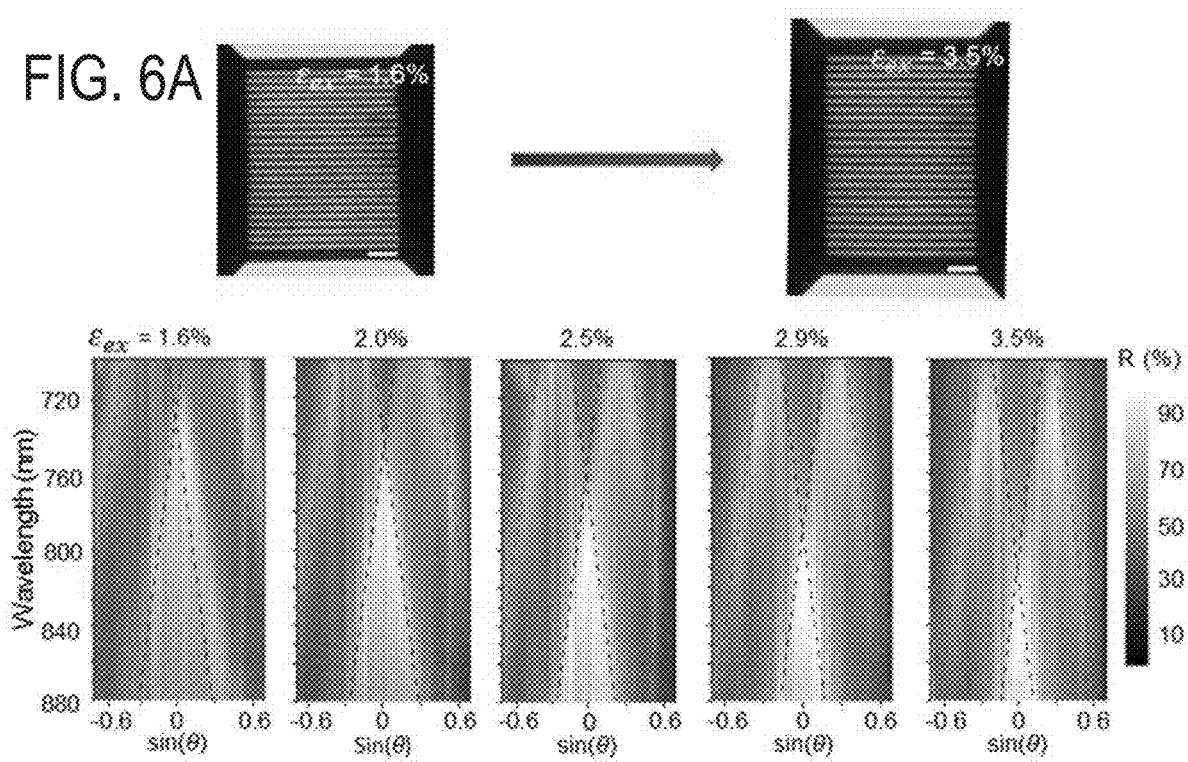
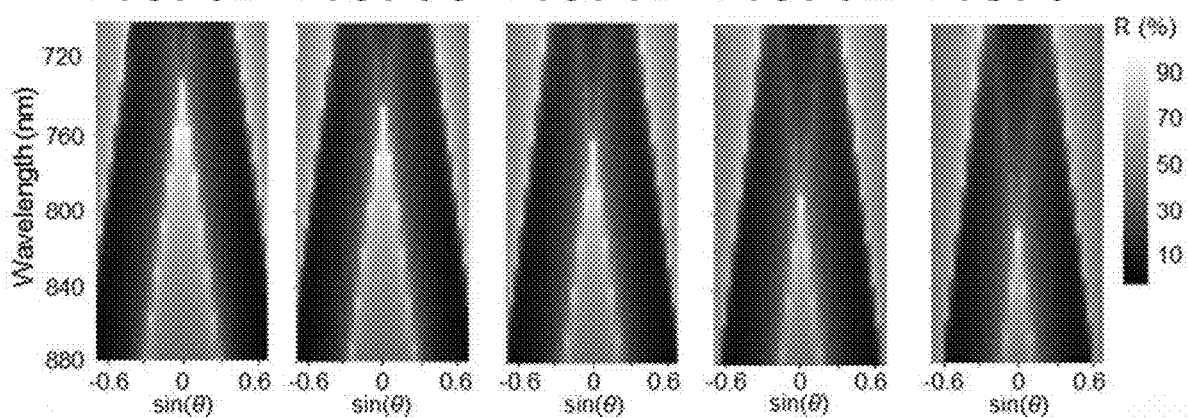
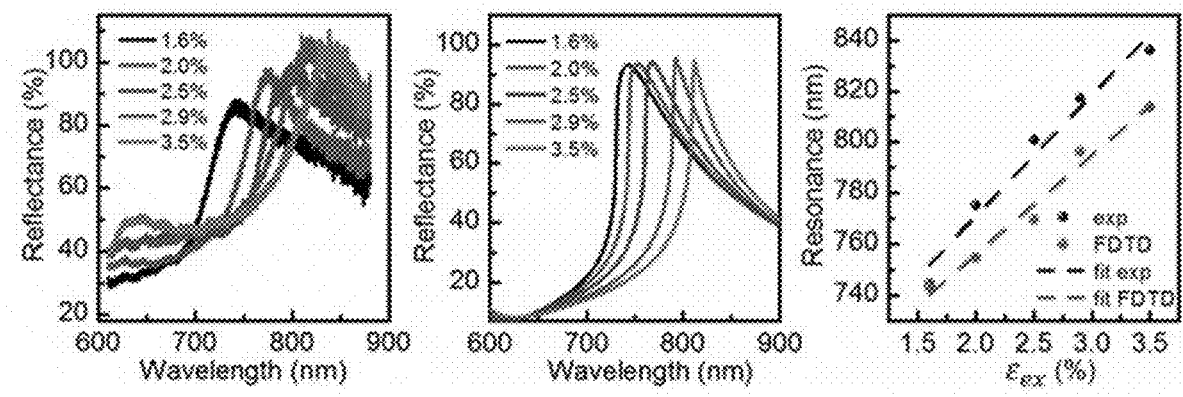
FIG. 6A FIG. 6B FIG. 6C FIG. 6D FIG. 6E FIG. 6F FIG. 6G FIG. 6H FIG. 6I FIG. 6J FIG. 6K FIG. 6L FIG. 6M FIG. 6N

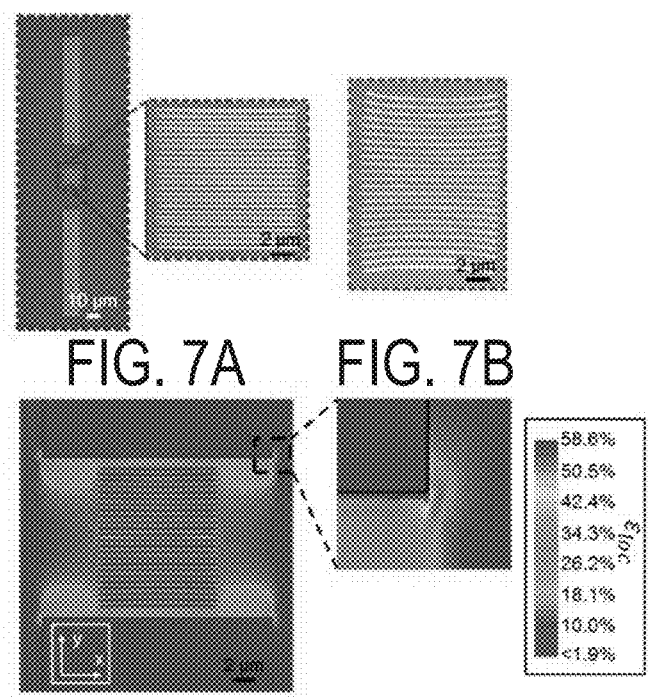
FIG. 7A  FIG. 7B
FIG. 7C
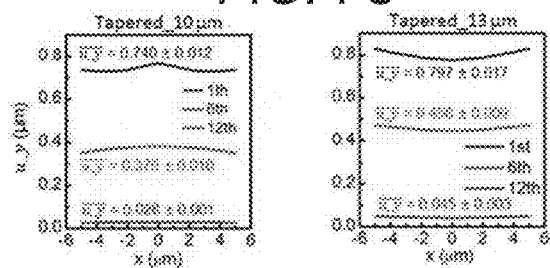
FIG. 7D  FIG. 7E
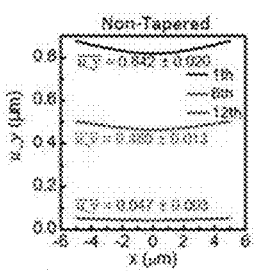 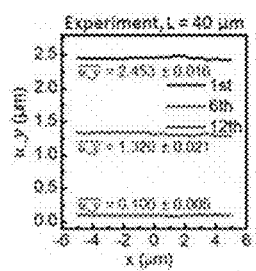
FIG. 7F  FIG. 7G
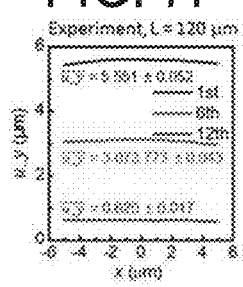
FIG. 7H

ULTRA-SENSITIVE, MECHANICALLY-RESPONSIVE OPTICAL METASURFACES VIA STRAIN AMPLIFICATION

RELATED APPLICATIONS

The present application claims priority to and the benefit of U.S. provisional application No. 62/904,784, "Ultra-Sensitive, Mechanically-Responsive Optical Metasurfaces Via Strain Amplification" (filed Sep. 24, 2019), the entirety of which application is incorporated herein by reference for any and all purposes.

GOVERNMENT RIGHTS

This invention was made with government support under Contract No. CMMI-1562884, awarded by the National Science Foundation and under Contract No. CMMI-1463344, awarded by the National Science Foundation. The government has certain rights in the invention.

TECHNICAL FIELD

The present disclosure relates to the field of strain-sensitive materials.

BACKGROUND

Recent work has considered reconfigurable platforms in which the external stimuli, such as voltage, strain, temperature, and light, dynamically change the distance between the plasmonic scatters and/or the optical constant of the medium. Existing approaches, however, exhibit comparatively low sensitivity. Accordingly, there is a need in the art for improved strain-sensitive materials, platforms, and devices.

SUMMARY

In meeting the described needs in the art, provided here are strain-sensitive components, which components are suitable for inclusion in a variety of technologies.

In one exemplary embodiment, the disclosed materials demonstrate strain amplification in microstructured polydimethylsiloxane (PDMS) substrates to create highly-sensitive, linearly-dependent, and reversibly-stretchable optical metasurfaces. The amplified strain on the optical metasurfaces is engineered by the geometry of a pair of microrods, which leads to significant enhancement of the mechano-sensitivity of the metasurfaces.

The disclosed technology can be used to, e.g., accommodate a variety of optical metasurfaces, including optical resonators, filters, gratings, waveplates, metalens, holograms, color pixels, and even nanolasers. The disclosed components can also be, e.g., integrated with piezoresistive materials to provide amplified mechano-sensitivity for stretchable electronics, of interest for human motion sensors and skin-mountable devices, as well as stretchable optics and electronics.

In one aspect, the present disclosure provides a mechanically responsive component, comprising: an elastic substrate, a first elongate microbody disposed on the elastic substrate, the first elongate microbody defining a major axis, a proximal end, and a distal end, the first elongate microbody defining a maximum width measured perpendicular to the major axis, and the width of the first elongate microbody measured at the proximal end being less than the maximum width, a second elongate microbody disposed on the elastic substrate, the second elongate microbody defining a major axis, a proximal end, and a distal end, the proximal end of the first elongate microbody being disposed opposite the proximal end of the second elongate microbody so as to define a gap between the proximal end of the first elongate microbody and the proximal end of the second elongate microbody; and a strain-sensitive structure disposed on the elastic substrate, the strain-sensitive structure being disposed in the gap between the proximal end of the first elongate microbody and the proximal end of the second elongate microbody, and the component being configured so as locally amplify, at the location of the strain-sensitive structure, an external strain applied to the elastic substrate.

In another aspect, the present disclosure provides a device, the device comprising a component according to the present disclosure.

Also provided are methods, comprising: exerting a strain on a component according to the present disclosure, wherein the strain-sensitive structure converts the strain to a signal.

Further provided are methods, comprising: exerting a strain on a component according to the present disclosure so as to effect a change in an optical property of the strain-sensitive structure.

Also provided are methods, comprising: exerting a strain on a component according to the present disclosure so as to effect a change in an electrical property of the strain-sensitive structure.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

In the drawings, which are not necessarily drawn to scale, like numerals may describe similar components in different views. Like numerals having different letter suffixes may represent different instances of similar components. The drawings illustrate generally, by way of example, but not by way of limitation, various aspects discussed in the present document. In the drawings:

FIGS. 1A-1D provide exemplary design and finite element (FE) modeling of the plasmonic grating and microrod metastructures. FIG. 1A provides a schematic of the fabrication process used to construct Au plasmonic gratings in the gap between a pair of mirror-symmetric, tapered microrods on PDMS substrates. EBL: electron beam lithography. FIG. 1B provides design parameters of metastructures. The inset defines x- and y-directions. $\varepsilon_{ex}$ is defined as the external strain applied across the two ends of the PDMS substrate in the y-direction. FIG. 1C provides exemplary scanning electron microscopy (SEM) images of a metastructure on a PDMS substrate with increasing magnification of the microrod gap and the plasmonic grating at $\varepsilon_{ex}$=0%. (d) FE modeling of the strain distribution on the metastructure on the surface of the PDMS substrate at $\varepsilon_{ex}$=3%. The magnified view shows the strain distribution in the region of the plasmonic grating. The color scale represents the local strain in the y-direction on the PDMS surface ($\varepsilon_{loc}$).

FIGS. 2A-2I provide exemplary strain amplification on metastructures with different G. Optical microscope images of the metastructures on the PDMS substrate with different designs of G: infinity (or no microrods) (FIG. 2A, FIG. 2B), 120 μm (FIG. 2C, FIG. 2D), 60 μm (FIG. 2E, FIG. 2F), and 16 μm (FIG. 2G, FIG. 2H) at $\varepsilon_{ex}$=0% (FIG. 2A, FIG. 2C, FIG. 2E, FIG. 2G) and at $\varepsilon_{ex}$=11.8% (FIG. 2B, FIG. 2D, FIG. 2F, FIG. 2H). Other design parameters of the metastructures are kept approximately the same as in FIG. 1C. The percent change of the grating pitch $$\left( I_{pitch} = \frac{p' - p}{p} \right)$$

is denoted in me figures for different metastructures. The white scale bar=20 μm and the red scale bar=2 μm. FIG. 2I provides a histogram of $A_{strain}$ (black) and $A_{sensitivity}$ (red) for microrod designs with varying G. Fitting of $$A_{strain} = 28.38 \times \exp\left(\frac{-G}{13.28}\right) + 1.70 \text{ (dashed black line) and}$$

$$A_{sensitivity} = 15.09 \times \exp\left(\frac{-G}{13.98}\right) + 1.00 \text{ (dashed red line)}$$

with an r-square at or above 0.996.

FIGS. 3A-3I provides strain amplification on metastructures with different L. Optical microscope images of the metastructures with a fixed G of 16 μm and varying L: 0 μm (FIG. 3A, FIG. 3B), 40 μm (FIG. 3C, FIG. 3D), 80 μm (FIG. 3E, FIG. 3F), 120 μm (FIG. 3G, FIG. 3H) for $\varepsilon_{ex}$=0% (FIG. 3A, FIG. 3C, FIG. 3E, FIG. 3G) and for $\varepsilon_{ex}$=11.8% (FIG. 3b, FIG. 3d, FIG. 3f, FIG. 3h). Other design parameters of the metastructures are kept approximately the same as in FIG. 1C. $I_{pitch}$ is denoted in the figures for different metastructures. White scale bar=20 μm and red scale bar=2 μm. FIG. 3i provides a histogram of $A_{strain}$ (black) and $A_{sensitivity}$ (red) for microrod designs with varying L. Fitting of $A_{strain}$=0.12×L+1.01 (dashed black line) and $A_{sensitivity}$=0.07×L+0.69 (dashed red line) with an r-square of 0.99.

Figure 4A:
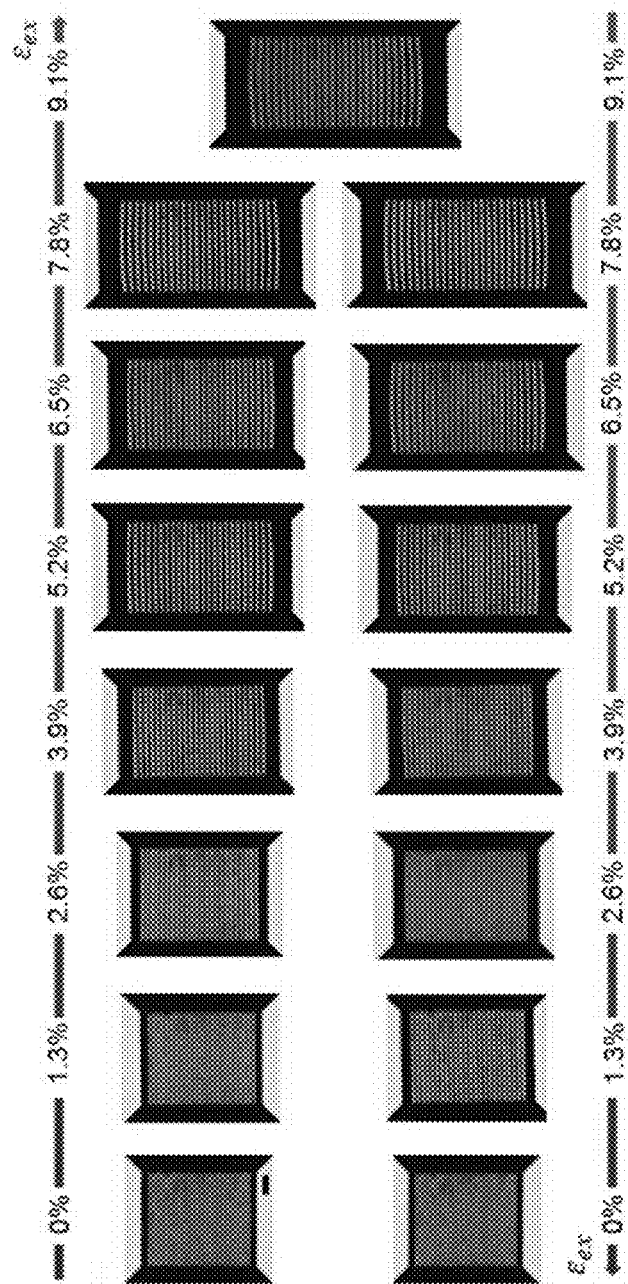
Figure 4B:
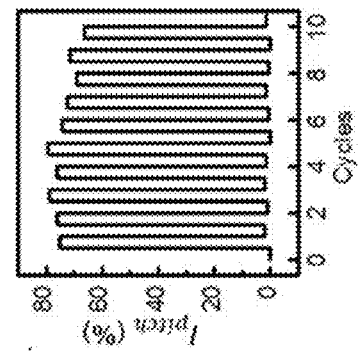
Figure 4C:
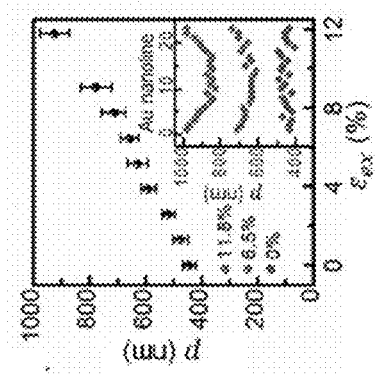
Figure 4D:
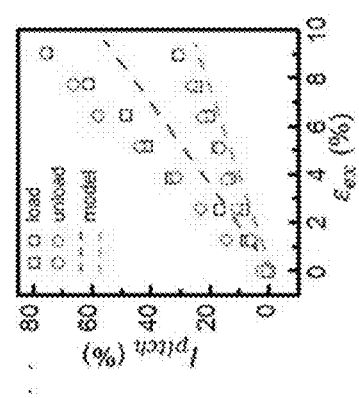

FIGS. 4A-4D provide exemplary mechanical responses of metastructures under continuous loading and unloading of $\varepsilon_{ex}$. FIG. 4A provides optical microscope images of the plasmonic grating with microrods of L=120 μm and G=16 μm at various $\varepsilon_{ex}$. Scale bar=2 μm. FIG. 4B provides $I_{pitch}$ as a function of $\varepsilon_{ex}$ for metastructures with G=16 μm and with L=120 μm (experiment: black, red symbols; FE model: purple line) and 40 μm (experiment: blue, green symbols; FE model: orange line). FIG. 4C provides p as a function of $\varepsilon_{ex}$ and (inset) the spacing between neighboring pairs of Au nanolines as a function of the sequence of Au nanolines in the grating counting from top to bottom at $\varepsilon_{ex}$=0% (blue dots), 6.5% (green dots), and 11.8% (red dots). FIG. 4D provides $I_{pitch}$ for the metastructure with L=120 μm and G=16 μm as it is cyclically stretched and released 10 times.

Figure 5A:
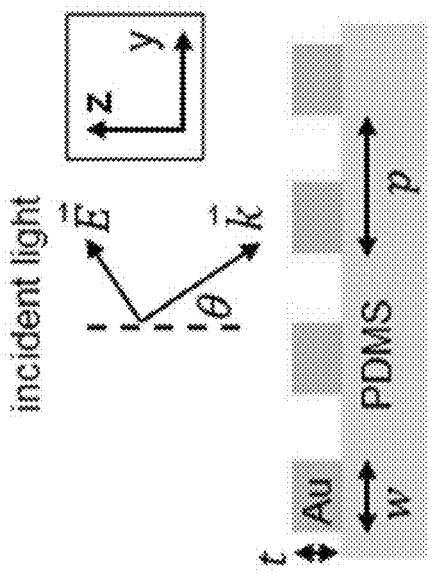
Figure 5C:
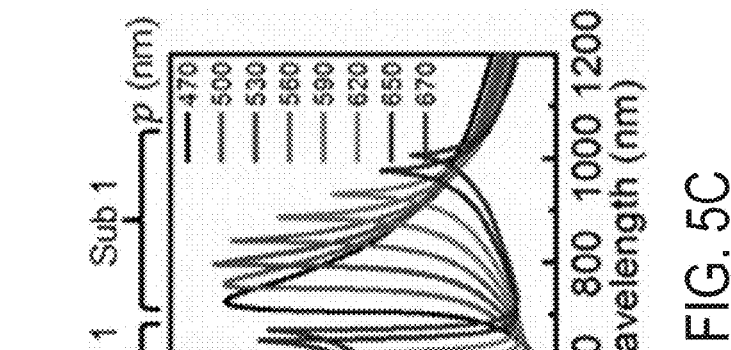
Figure 5B:
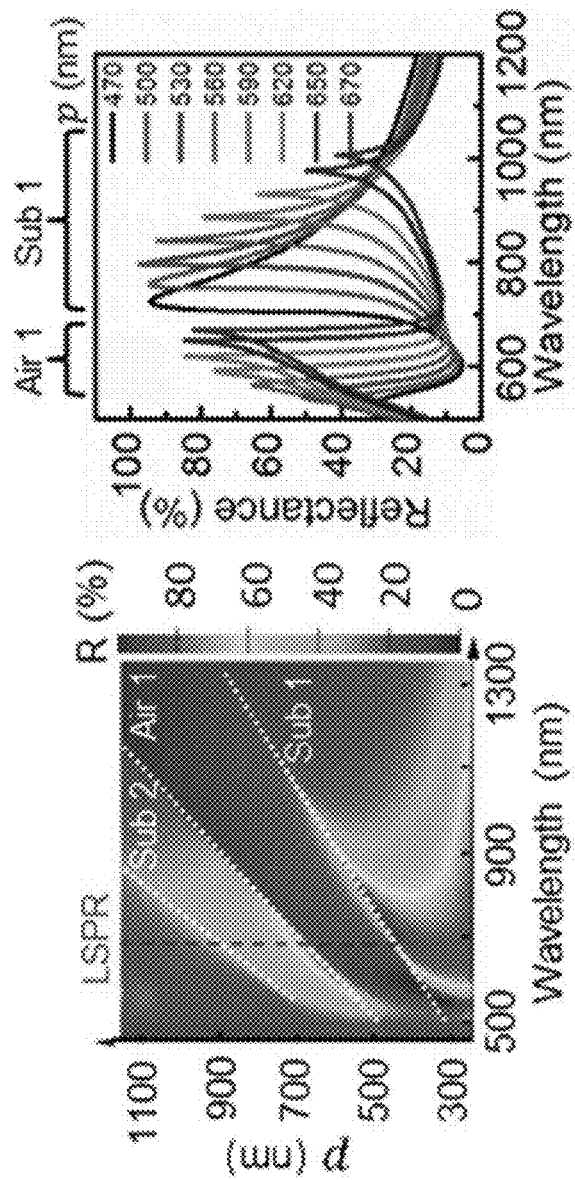

FIGS. 5A-5C provide simulated optical responses of the plasmonic grating. FIG. 5A provides a schematic of the plasmonic grating used in Finite-Difference Time-Domain (FDTD) simulations. The incident light is linearly polarized in the y-z plane. FIG. 5B provides FDTD simulations of the dispersion diagram for the reflectance spectra of the plasmonic grating at normal incidence as a function of p. The first- and second-order substrate mode and the first-order air mode of $\lambda_D$ at θ=0° are plotted as white dashed lines and denoted by "Sub 1", "Sub 2", and "Air 1", respectively. The wavelength of the transverse localized surface plasmon resonance (LSPR) of the single Au nanoline is marked by a red dashed line. FIG. 5C provides FDTD simulations of the reflectance spectra of the plasmonic grating at θ=0° with p varying from 470 nm to 670 nm. The first-order substrate mode and first-order air mode of $\lambda_D$ are denoted as "Sub 1" and "Air 1", respectively.

FIGS. 6A-6N provide experimental and simulated reflectance spectra of the plasmonic grating under strain. FIG. 6A provides optical microscope images of the metastructures (L=120 G=16 μm) as $\varepsilon_{ex}$ is varied from 1.6% to 3.5% (images for intermediate $\varepsilon_{ex}$ in FIG. 17). Scale bar=2 FIGS. 6B-6F provide angle-resolved reflectance spectra of the plasmonic grating as a function of $\varepsilon_{ex}$, with angle-dependent first-order substrate mode and the first-order air mode of $\lambda_D$ marked (black and red dashed lines). FIGS. 6G-6K provide FDTD simulations of grating reflectance spectra with grating dimensions matched to those in FIGS. 6b-6f respectively. FIG. 6L provides experimental and (FIG. 6M) FDTD simulated reflectance spectra at normal incidence extracted from (FIGS. 6B-6F) and (FIGS. 6G-6K for various $\varepsilon_{ex}$. FIG. 6N provides reflectance peak positions at normal incidence from experiment (black dot) and simulation (red dot) for various $\varepsilon_{ex}$ and their linear fitting (black and red dashed lines), with r-square at or above 0.96 (details in Supporting Information).

FIGS. 7A-7H provide non-uniform strain distribution at the corners and edges of the microrods. FIG. 7A provides SEM images of a pair of microrods with L=80 μm, B=0, W=12 μm, T=40 nm, and G=50 μm. The magnified SEM image in the gap area shows a plasmonic grating with l=12 μm, w=140 nm, and t=40 nm on a pitch p=470 nm. The width of the microrod is designed to be the same as the length of the Au nanolines, i.e., $$\frac{W}{l} = 1.$$

FIG. 7B provides that for $\varepsilon_{ex}$=30% is applied to the PDMS substrate. The Au nanolines at the top and the bottom of the plasmonic grating bend in the shape of an arc. FIG. 7C provides that for $\varepsilon_{ex}$=3%, FE simulation shows the strain distribution on the surface of PDMS substrate for the non-tapered microrod $$\left( A = 20 \text{ μm}, \frac{W}{l} = 2 \right).$$

The magnified image shows "hot spots" of the extremely high local strain at the corners of the microrods. The color scale represents the local strain in the y-direction on the PDMS surface ($\varepsilon_{loc}$). The displacement of the $1^{st}$, $6^{th}$, and $12^{th}$ Au nanolines in the grating (counting from top to bottom) at $\varepsilon_{ex}$=3% for the tapered microrod with 10 μm topline (A=10 μm FIG. 7D), the tapered microrod with 13 μm topline (A=13 FIG. 7E), and non-tapered microrod (A=FIG. 7F) based on FE modeling. u_y of the experimentally fabricated Au nanolines at $\varepsilon_{ex}$ 11.8% for the microrods with L=40 G=16 μm (FIG. 7G) and L=120 G=16 μm (FIG. 7H). The average displacement (u_ȳ) of the Au nanolines and the standard errors are indicated in the figure.

Figure 8A:
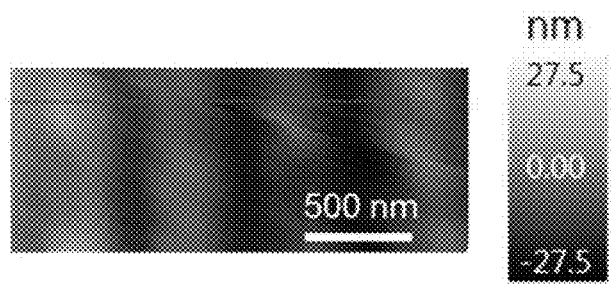
Figure 8B:
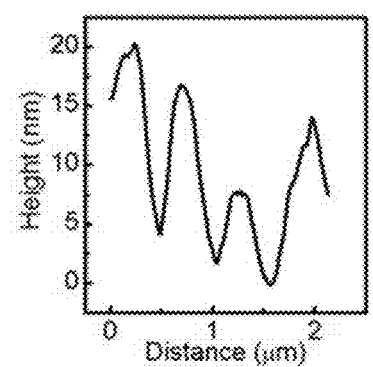
Figure 8C:
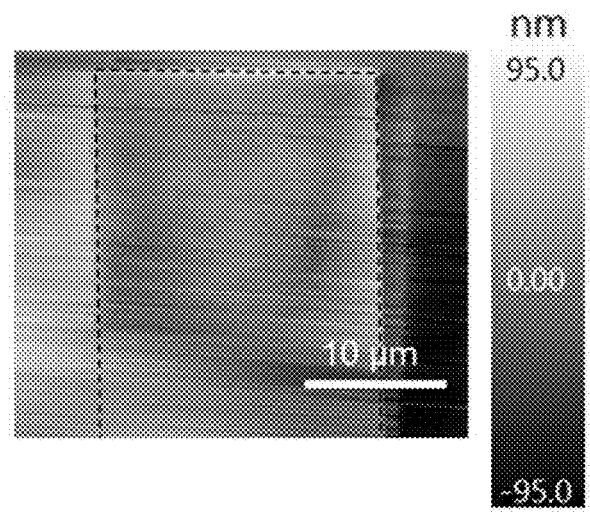
Figure 8D:
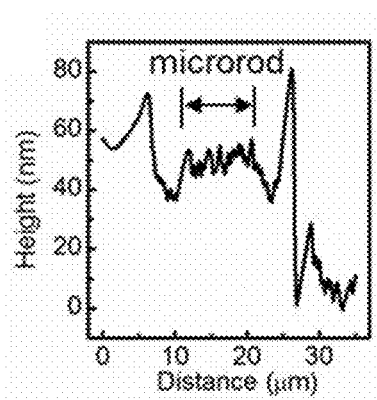

FIG. 8A provides an atomic force microscope (AFM) image of the grating and (FIG. 8B) the corresponding height profile along the horizontal red line. FIG. 8C provides an AFM image of the microrod (marked by dashed lines) and (FIG. 8D) the corresponding height profile along the horizontal red line. The roughness of the Au layer on PDMS is approximately 3 nm according to the line cut analysis of the microrod (FIG. 8D).

Figure 9B:
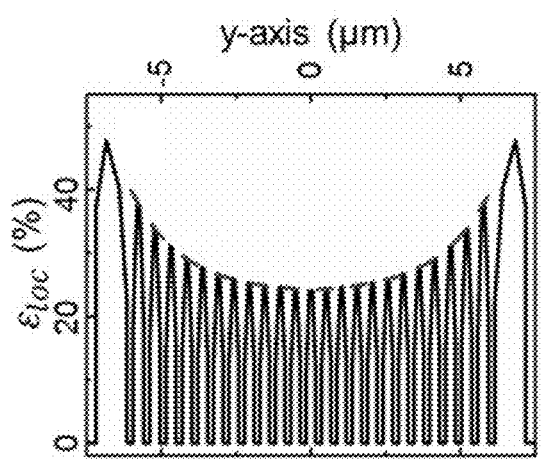
Figure 9A:
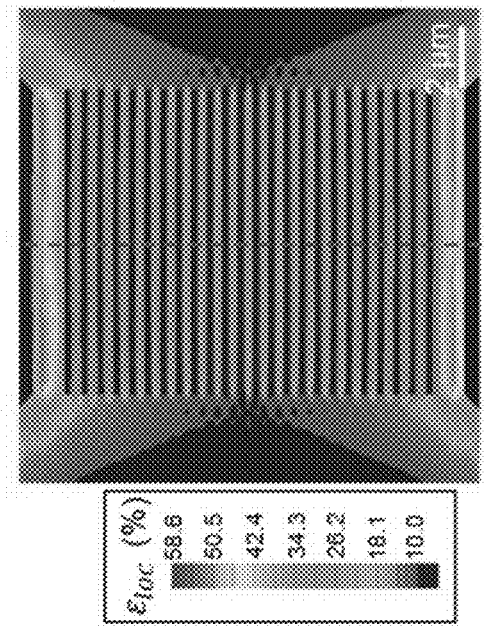

FIGS. 9A-9B provide a magnified view of the distribution of $\varepsilon_{loc}$ in the plasmonic grating region. FIG. 9A provides FE modeling of $\varepsilon_{loc}$ on the surface of a PDMS substrate with $\varepsilon_{ex}$=3%. The dimensions of the modeled metastructure are the same as those in FIG. 1C, 1D. FIG. 9B provides the profile of $\varepsilon_{loc}$ along the (red) dashed line in FIG. 9A. $\varepsilon_{spacing}$ in the plasmonic grating is fit with an exponential function, $$\varepsilon_{loc} = 23.73 + 0.46 \times \exp\left(\frac{|y|}{1.69}\right),$$

with an r-square above 0.999 (blue dashed line).

Figures 10A, 10B:
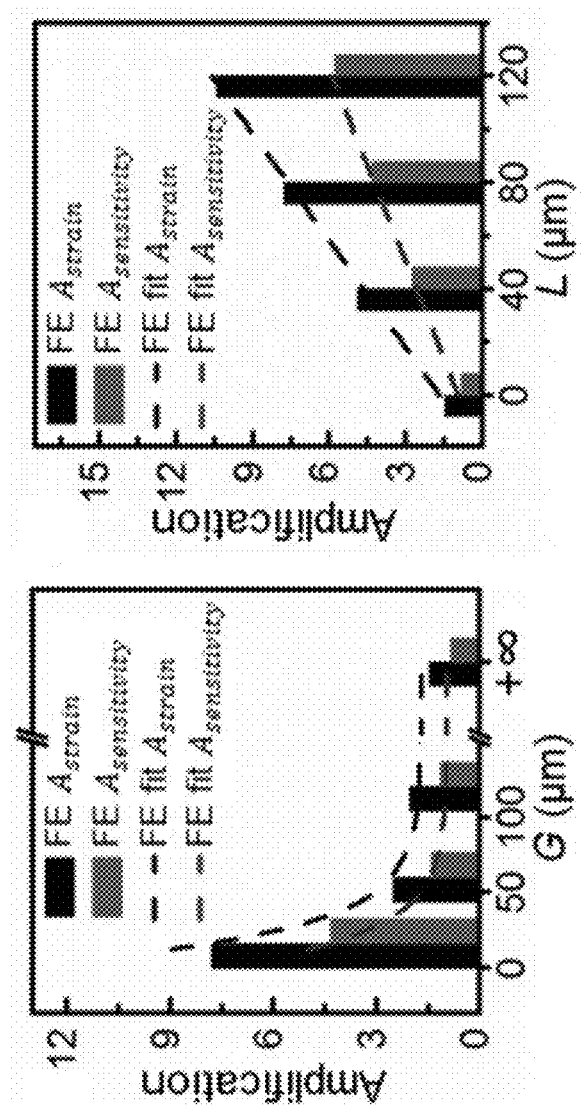

FIGS. 10A-10B provide $A_{strain}$ and $A_{sensitivity}$ obtained from FE models for metastructures with various G and L at $\varepsilon_{ex}$=11.8%. FIG. 10A provides $A_{strain}$ and $A_{sensitivity}$ as a function of G with L fixed at 80 Fitting of $$A_{strain} = 12.30 \times \exp\left(\frac{-G}{22.71}\right) + 1.70 \text{ (black dashed line) and}$$

$$A_{sensitivity} = 6.83 \times \exp\left(\frac{-G}{22.71}\right) + 0.94 \text{ (red dashed line),}$$

with r-square of 0.98. FIG. 10B provides $A_{strain}$ and $A_{sensitivity}$ as a function of L with G fixed at 16 Fitting of $A_{strain}$=0.07×L+1.67 (black dashed line) and $A_{sensitivity}$=0.04×L+0.93 (red dashed line), with r-square of 0.995.

Figure 11:
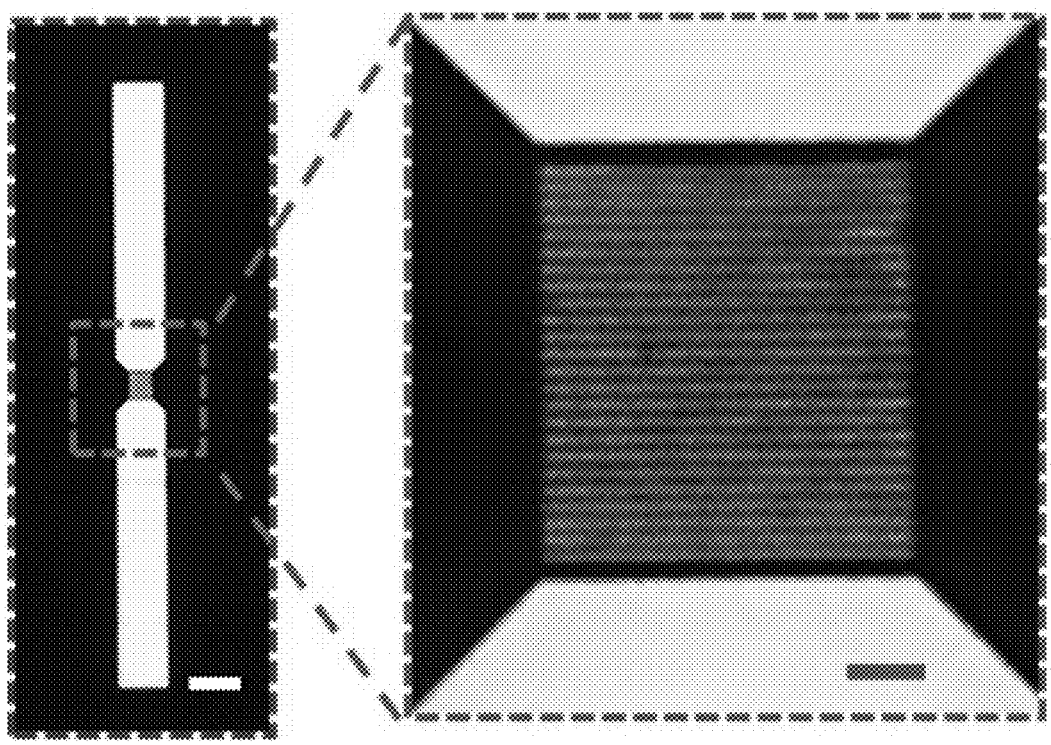

FIG. 11 provides a representation of a metastructure released from strain. Optical microscope image of the metastructure with G=16 μm and L=120 μm after the PDMS is released from $\varepsilon_{ex}$ 11.8%. White scale bar=20 μm and red scale bar=2 μm.

Figure 12:
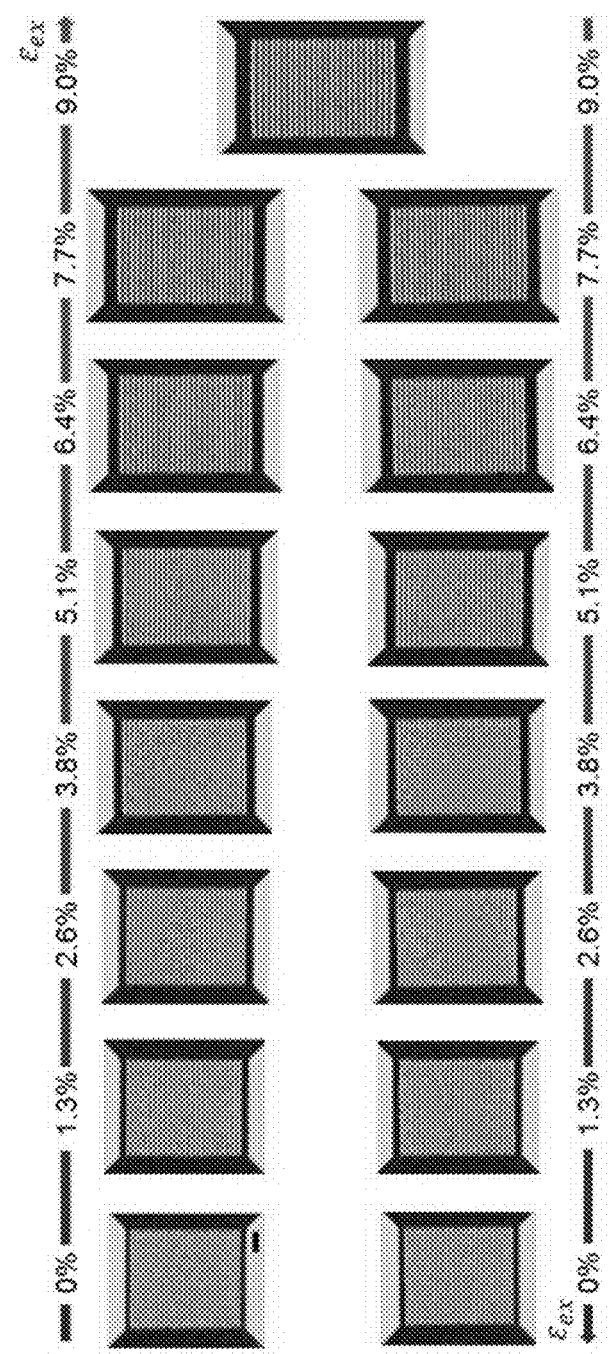

FIG. 12 provides example mechanical responses of metastructures under continuous loading and unloading of $\varepsilon_{ex}$. Optical microscope images of the metastructure with G=16 μm and L=40 μm at various $\varepsilon_{ex}$. The applied $\varepsilon_{ex}$ is denoted on top or on bottom of each figure, increasing from 0% to 9.0% and decreasing from 9.0% to 0% in steps of approximately 1.3%. Scale bar=2 μm.

Figures 13A, 13B:
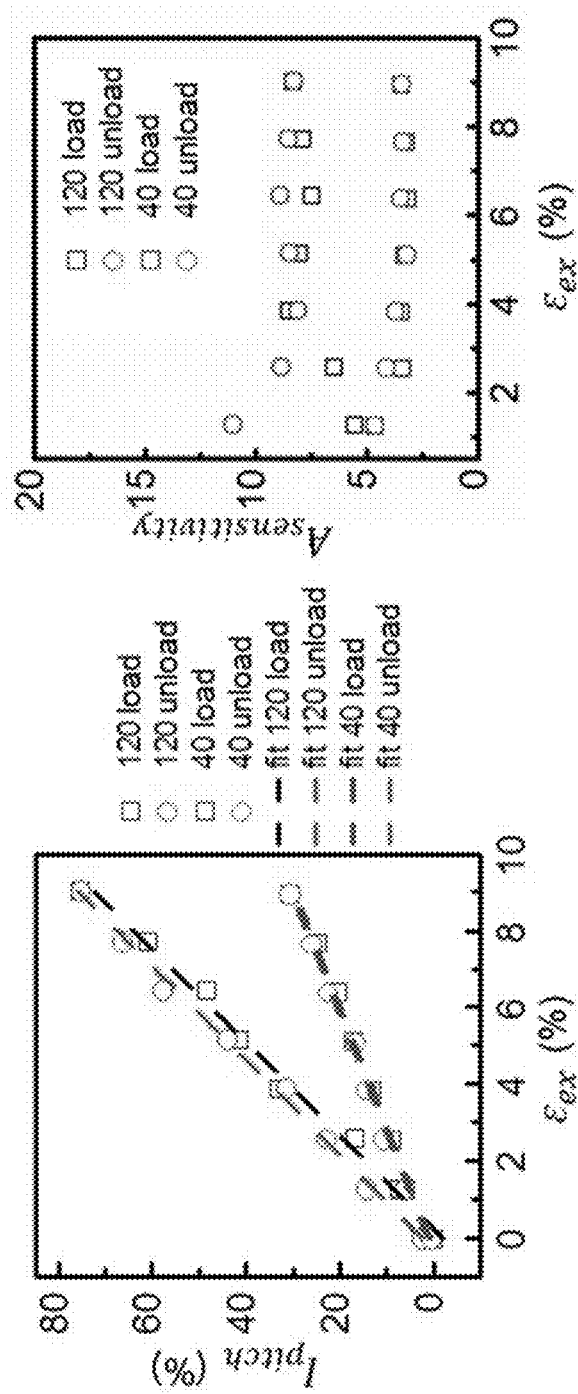

FIG. 13A provides an example fitting of mechanical responses of metastructures. The linear fitting of $I_{pitch}$ as a function of $\varepsilon_{ex}$ (%) for the metastructures with G=16 μm and with L=120 μm (black, red symbols) and 40 μm (blue, green sFymbols). Square (circle) symbols are for loading (unloading) strain. The linear fitting results are: $I_{pitch}$=8.3×$\varepsilon_{ex}$×100−2.1, black dashed line; $I_{pitch}$=8.2×$\varepsilon_{ex}$×100+2.3, red dashed line; $I_{pitch}$=3.2×$\varepsilon_{ex}$×100+0.6, blue dashed line; $I_{pitch}$=3.2×$\varepsilon_{ex}$×100+1.3, green dashed line. The r-square for all the fittings are at or above 0.99. FIG. 13B provides $A_{sensitivity}$ plotted as a function of $\varepsilon_{ex}$ for the metastructures with G=16 μm and with L=120 μm (black, red symbols) and 40 μm (blue, green symbols).

Figure 14:
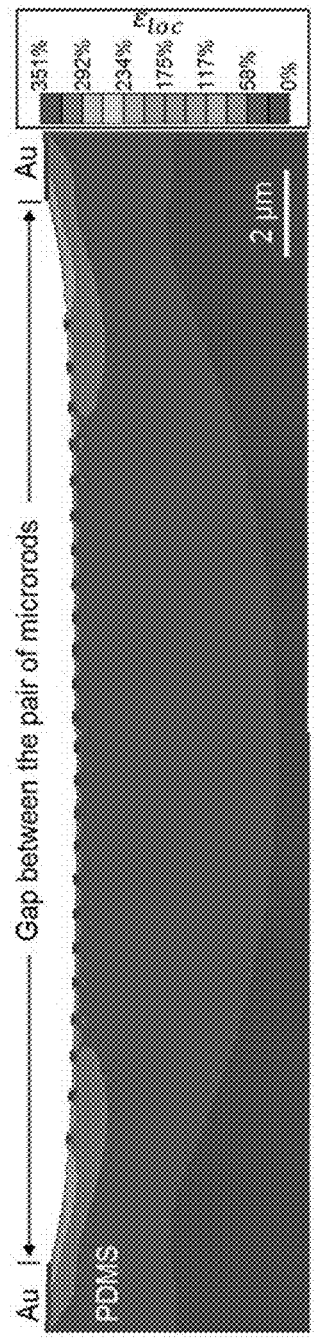

FIG. 14. The cross-sectional image of the Au nanolines on PDMS substrate at $\varepsilon_{ex}$=11.8% by FE modeling.

Figure 15B:
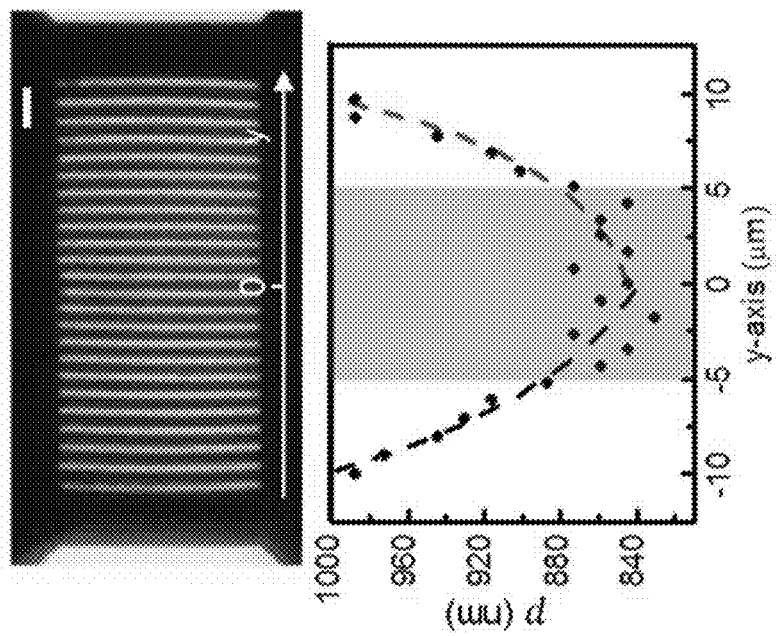
Figure 15A:
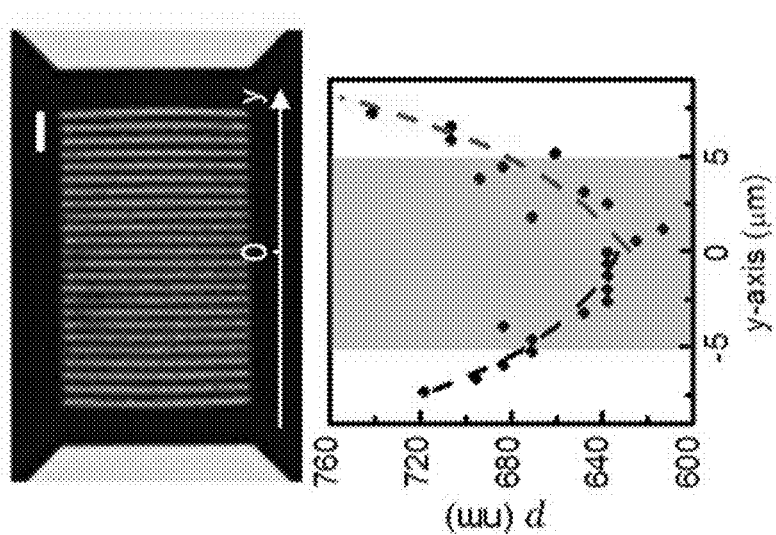

FIGS. 15A-15B provides optical images and quantitative analyses of the spacing between neighboring Au nanolines in the plasmonic grating. The metastructure design is G=16 μm and L=120 μm. The spacing between the neighboring Au nanolines in y<0 and y>0 regions are plotted along the y-axis and fit with the exponential function at $\varepsilon_{ex}$=6.5% (FIG. 16A) and $\varepsilon_{ex}$=11.8% (FIG. 16).

$$p = 19.7 \times \exp\left(-\frac{y}{4.5}\right) + 612.6, \quad (a)$$

r−square = 0.88 (black dished line) and $$p = 31.1 \times \exp\left(\frac{y}{4.9}\right) + 597.1,$$

r−square = 0.73 (red dished line).

$$p = 37.7 \times \exp\left(-\frac{y}{6.0}\right) + 799.5, \quad (b)$$

r−square = 0.91 (black dashed line) and $$p = 13.8 \times \exp\left(\frac{y}{3.8}\right) + 830.1,$$

r−square = 0.90 (red dashed line).

The pink region indicates the center area of the grating (10 μm×10 μm). In the center area, the standard deviation in p' is 23 nm for $\varepsilon_{ex}$=6.5% and 16 nm for $\varepsilon_{ex}$=11.8%, which are comparable to the fabrication tolerance at $\varepsilon_{ex}$=0%. Scale bar=2 μm.

Figure 16C:
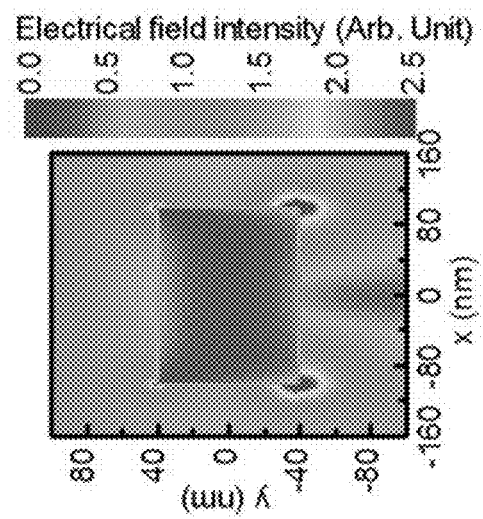
Figure 16B:
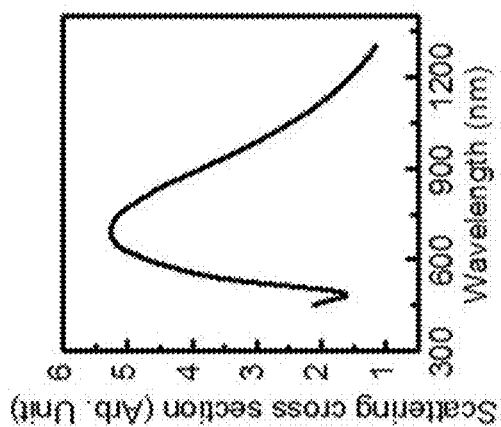
Figure 16A:
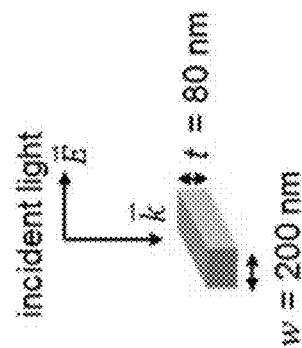

FIGS. 16A-16C provide a FDTD simulation of the optical response of an individual Au nanoline. FIG. 16A provides a schematic of the individual Au nanoline used in FDTD simulations. The width and the thickness of the nanoline are set to the same dimensions as those in experiments (FIG. 1C, FIG. 1D). The incident light is linearly polarized along the transverse direction of the nanoline. FIG. 16B provides a FDTD simulation result for the scattering cross section of the individual Au nanoline. FIG. 16C provides an electrical field intensity map in the cross-sectional plane of an individual Au nanoline at 693 nm wavelength. The transverse section of the Au nanoline is positioned in the center of the map.

Figures 17A, 17B, 17C, 17D, 17E:
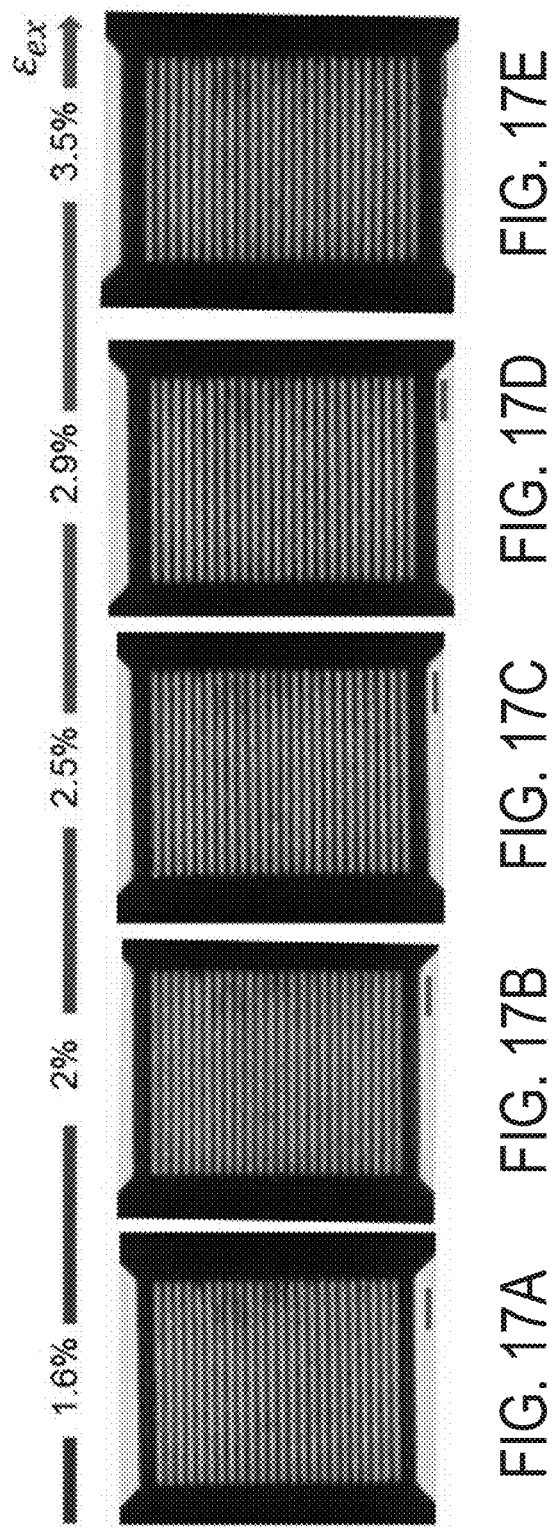

FIG. 17 provides an example metastructure under $\varepsilon_{ex}$ variations. Optical microscope images of the metastructure with G=16 μm and L=120 μm when the $\varepsilon_{ex}$ is gradually varied from 1.6% (a) to 2.0% (b), 2.5% (c), 2.9% (d), and 3.5% (e). Scale bar=2 μm.

Figure 18:
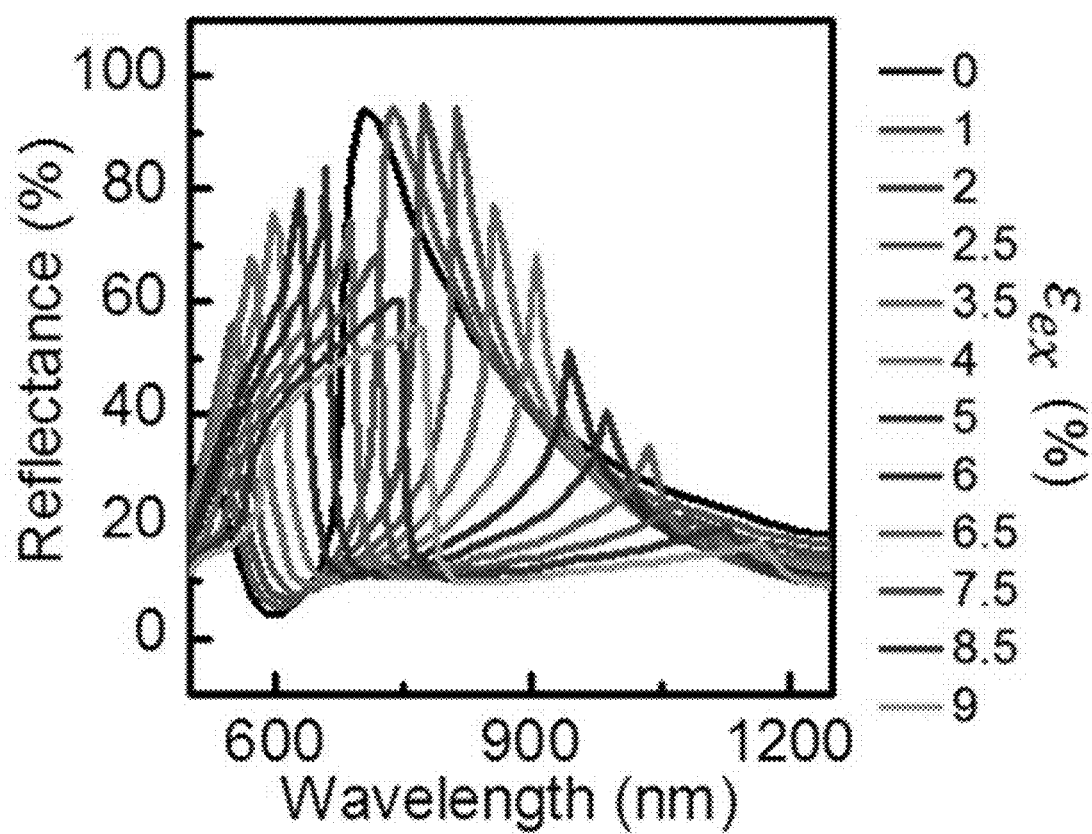

FIG. 18 provides FDTD simulation results for the reflectance spectra of the plasmonic grating. In the simulation, the plasmonic grating has a width w=200 nm, a thickness t=80 nm, and a p varying from 440 nm to 770 nm in steps of 30 nm. Light is at normal incidence with y-polarization. p is directly related with $\varepsilon_{ex}$ applied to the metastructure. p varying from 440 nm to 770 nm approximately corresponds to $\varepsilon_{ex}$ varying from 0% to 9% based on the fitting equation in FIG. 13A (black dashed line).

Figure 19:
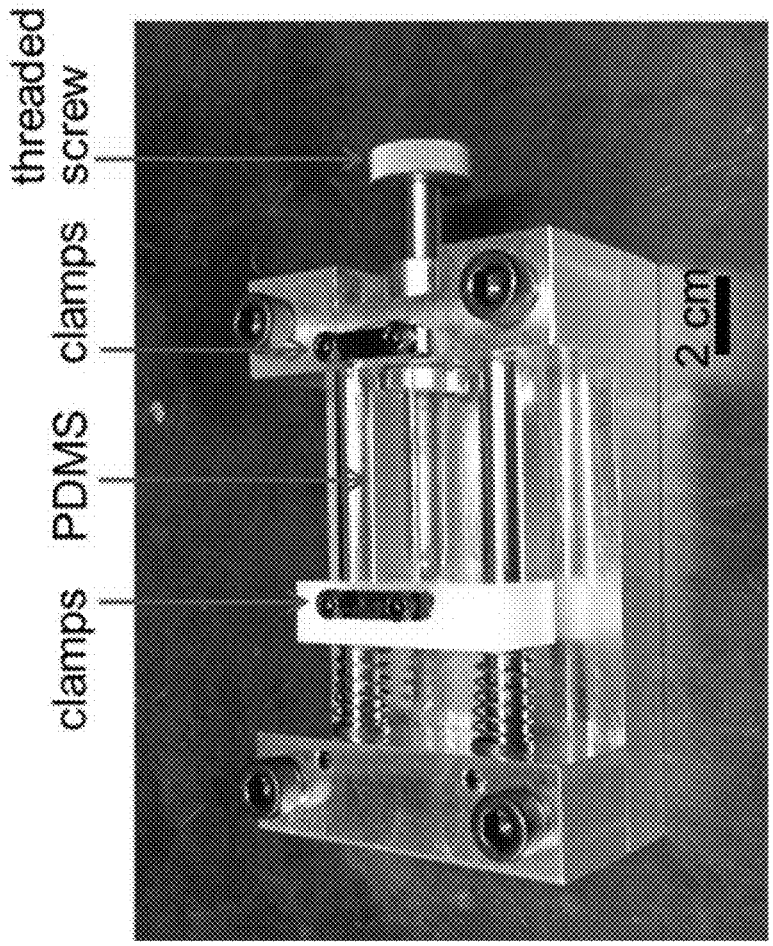

FIG. 19 provides a view of the mechanical stretcher used to apply external strain to the metastructures. The PDMS substrate is fixed by two clamps on the stage and a threaded screw is rotated to apply the external strain.

Figure 20:
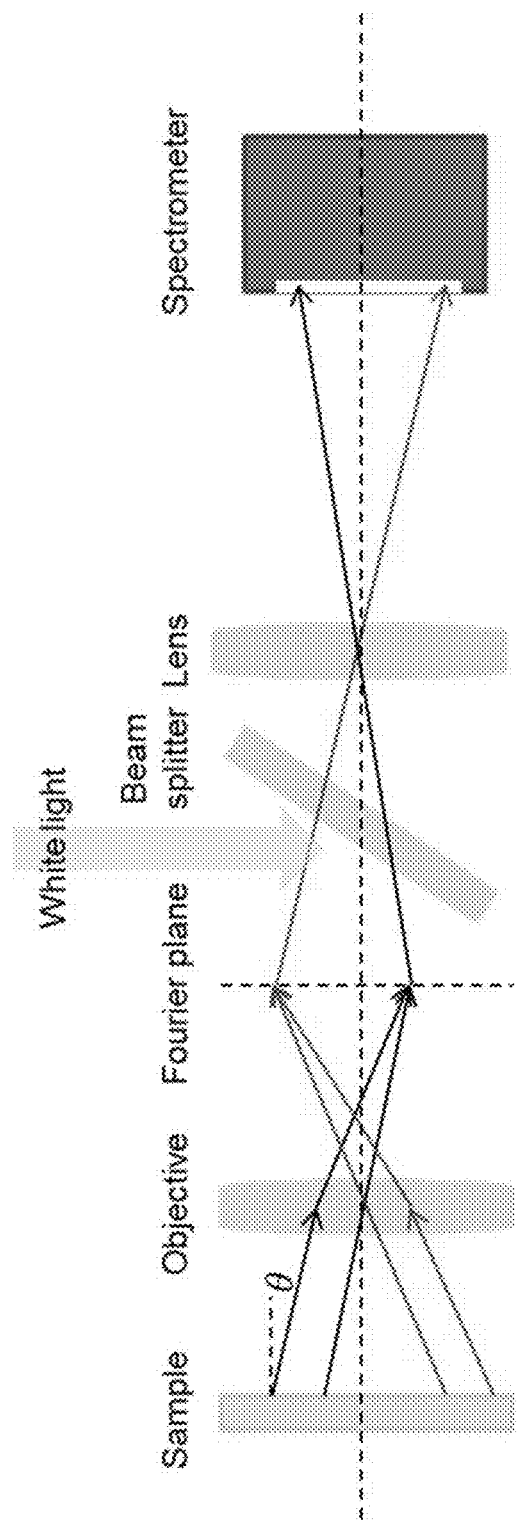

FIG. 20 provides a schematic of the home-built angle-resolved reflectance measurement system.

Figure 21:
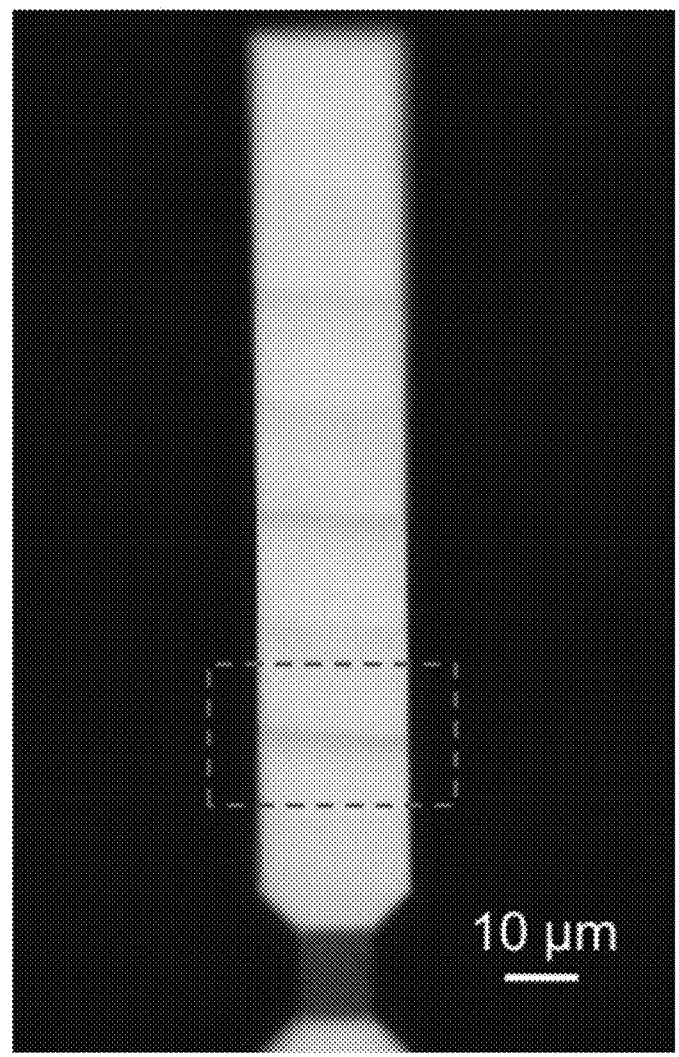

FIG. 21 illustrates buckling effect on example microrods. Microscope image of the metastructure with G=16 μm and L=120 μm after stretching and releasing between $\varepsilon_{ex}$=9.1% and $\varepsilon_{ex}$=0% cyclically for 10 times. The red dashed rectangular indicates an area of the microrod that shows buckling after cyclical stretching.

Figure 22A:
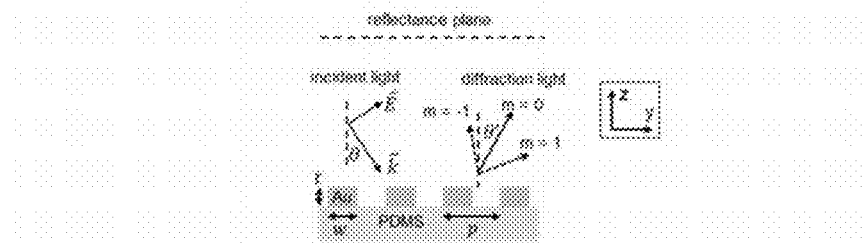
Figure 22B:
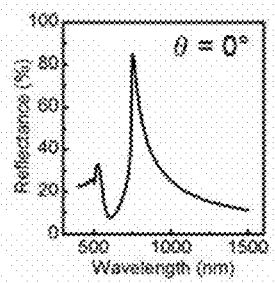
Figure 22C:
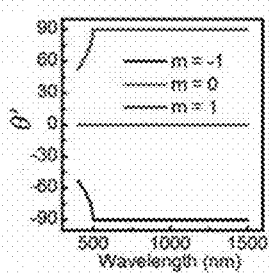
Figure 22D:
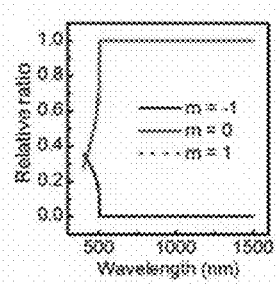
Figure 22E:
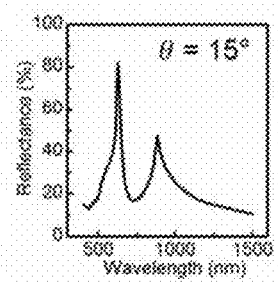
Figure 22F:
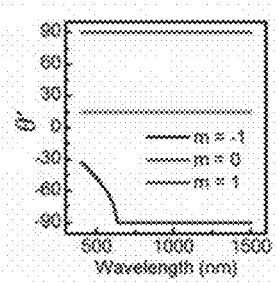
Figure 22G:
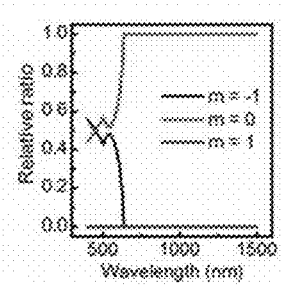
Figure 22H:
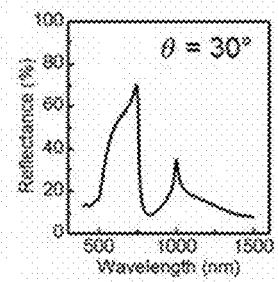
Figure 22I:
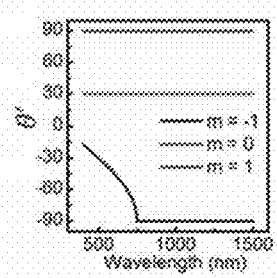
Figure 22J:
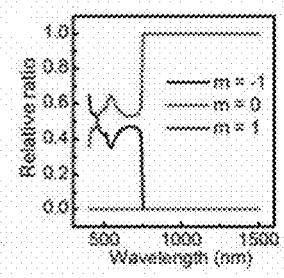
Figure 22K:
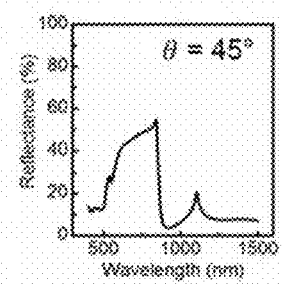

FIG. 22A provides a schematic showing the incident angle (θ), angle of different diffractive orders (θ'), and the reflectance plane for the Au plasmonic grating on the PDMS substrate used in FDTD simulations. The reflectance plane collects all the diffractive orders in the reflectance angle from −90° to 90°. For θ=0°, FIG. 22B provides the reflectance of the plasmonic grating. FIG. 22C provides the angle of different diffractive orders. FIG. 22D provides the relative ratio of the intensity of the different diffractive orders in the reflectance light. FIG. 22E-FIG. 22G, FIG. 22H-FIG. 22J, and FIG. 22K-FIG. 22M are for θ=15°, 30°, and 45°, respectively.

DETAILED DESCRIPTION OF ILLUSTRATIVE EMBODIMENTS

The present disclosure may be understood more readily by reference to the following detailed description taken in connection with the accompanying figures and examples, which form a part of this disclosure. It is to be understood that this invention is not limited to the specific devices, methods, applications, conditions or parameters described and/or shown herein, and that the terminology used herein is for the purpose of describing particular embodiments by way of example only and is not intended to be limiting of the claimed invention.

Also, as used in the specification including the appended claims, the singular forms "a," "an," and "the" include the plural, and reference to a particular numerical value includes at least that particular value, unless the context clearly dictates otherwise. The term "plurality", as used herein, means more than one. When a range of values is expressed, another embodiment includes from the one particular value and/or to the other particular value. Similarly, when values are expressed as approximations, by use of the antecedent "about," it will be understood that the particular value forms another embodiment. All ranges are inclusive and combinable, and it should be understood that steps may be performed in any order.

It is to be appreciated that certain features of the invention which are, for clarity, described herein in the context of separate embodiments, may also be provided in combination in a single embodiment. Conversely, various features of the invention that are, for brevity, described in the context of a single embodiment, may also be provided separately or in any subcombination. All documents cited herein are incorporated herein in their entireties for any and all purposes.

Further, reference to values stated in ranges include each and every value within that range. In addition, the term "comprising" should be understood as having its standard, open-ended meaning, but also as encompassing "consisting" as well. For example, a device that comprises Part A and Part B may include parts in addition to Part A and Part B, but may also be formed only from Part A and Part B.

Three-dimensional metamaterials or analogous two-dimensional metasurfaces can be constructed by arranging sub-wavelength size- and shape-engineered plasmonic scatters to create artificial structures with exotic optical properties. Unlike conventional optical components where a substantial change in the amplitude, phase, or polarization of light is gradually accumulated over a distance, metasurfaces introduce significant modulation of light within nanometer scales as plasmonic scatters interact strongly with electromagnetic fields. By designing the spatial variation of the scatters and therefore their electromagnetic response, the wavefront of light can be modulated based on Huygen's principle.

One can create reconfigurable platforms in which the external stimuli, such as voltage, strain, temperature, and light, dynamically change the distance between the plasmonic scatters and/or the optical constant of the medium. Among them, modulating optical responses via strain applied to metasurfaces fabricated on elastomeric substrates integrates optical and mechanical functionalities. Achieving highly-sensitive, dynamically-tunable metasurfaces is important for the development of reconfigurable, flat optical components in optical sensing, imaging, and displays.

Provided here are, as an example, a general platform of microstructured elastomeric substrates that amplifies the mechano-sensitivity of metasurfaces. The microstructured elastomeric substrates can be constructed as a pair of mirror-symmetric, tapered microrods with opposing tips separated by a small distance on the surface of PDMS.

To demonstrate enhanced mechano-sensitivity, one can select the Au plasmonic lattice grating as an example optical metasurface that supports strong and narrow surface lattice resonances. One can position the plasmonic grating in the middle of the gap between the pair of microrods. Using FE mechanics modeling, one can map the strain distribution on the PDMS substrate and find the strain is zero in regions beneath and is significantly enhanced adjacent to the microrods.

By systematically changing the distance between and the length of the microrods, one can realize tailorable strain amplification on the metasurface. Exploiting an example microrod geometry that gives the highest strain amplification, an ultra-sensitive surface lattice resonance was achieved that shifts approximately 48 nm per 1% strain variation. The microstructured elastomeric substrate provides a platform to accommodate metasurfaces with various functionalities such as filters, waveplates, lenses, and holograms for ultra-sensitive, reconfigurable optics.

Integration of Optical Metasurfaces on Microstructured Elastomeric Substrates

FIG. 1A depicts the fabrication process developed to create microstructured PDMS substrates with integrated plasmonic lattice gratings. On top of a sacrificial Cu layer deposited on a silicon wafer, one can define a pair of mirror-symmetric, tapered microrods with a plasmonic grating in its gap via electron beam lithography and Au thermal evaporation. PDMS is cast and cured upon the microrods and the plasmonic grating, which one can call "metastructure" in short. The Cu layer is then removed using a Cu etchant, releasing the metastructure and leaving it embedded in the PDMS substrate.

FIG. 1B shows the design parameters of the metastructure. The width of the microrods (W) are designed to be two times greater than the length of the Au grating nanolines (l), i.e., $$\frac{W}{l} = 2,$$

to avoid non-uniform strain distributions generated at the corners of the microrods upon stretching (FIG. 7A, FIG. 7B). The ends of the microrods are tapered in the shape of a trapezoid to better concentrate strain in the gap between the pair of microrods and to alleviate bending of the Au nanolines under external strain ($\varepsilon_{ex}$) (FIG. 7C-7H). FIG. 1C shows SEM images of a representative structure of the microrods and the plasmonic gratings on a PDMS substrate at 0% external strain. The dimensions of the microrods are designed as L=80 μm in length, W=20 μm in width, and T=80 nm in thickness, with the ends toward the gap tapered as an isosceles trapezoid with topline A=10 μm and height B=5 μm. The gap between the pair of microrods is G=16 μm. The plasmonic grating is composed of 24 Au nanolines with length l=10 μm, width w=200 nm, and thickness t=80 nm on a pitch of p=500 nm. An atomic force microscope (AFM) image of the metastructure on PDMS is shown in FIG. 8.

FIG. 1D presents FE predictions of the strain distribution on the surface of the PDMS substrate when $\varepsilon_{ex}$ of 3% is applied in the y-direction, for a metastructure with the same dimensions as the experimentally fabricated structures shown in FIG. 1C. Since the microrods have much higher Young's modulus than the PDMS, the local strain in the y-direction ($\varepsilon_{loc}$) underneath the microrods is approximately 0%. Strain is transferred and concentrated at the plasmonic grating because the microrods and the plasmonic grating have significantly different dimensions along the direction of strain application. $\varepsilon_{loc}$ is highest (47.5%) in regions closest to the edges of the microrods where there is the largest change in local stiffness and exponentially attenuates into regions neighboring the microrods (FIG. 9). $\varepsilon_{loc}$ in spaces between the Au nanolines, which one can denote as $\varepsilon_{spacing}$, has an average value of 28.1%±4.2% (green regions in FIG. 1D), which is nearly 10 times larger than $\varepsilon_{ex}$. In all experiments and simulations, $\varepsilon_{ex}$ is uniaxial and applied in the y-direction.

Example Design Rules for Microrod Geometry

One can characterize the magnitude of the strain amplification on the plasmonic grating as one changes G from infinity (no microrods) to 120 µm, 60 µm, and 16 µm (FIG. 2), while keeping other dimensions of the metastructure approximately fixed to the design in FIG. 1C. At $\varepsilon_{ex}$=0%, for each G the fabricated plasmonic gratings on PDMS substrates have p±Δp of 513±22 nm, 512±20 nm, 512±13 nm, and 474±17 nm, respectively (FIGS. 2A, 2C, 2E, 2G). Only for the smallest G, a slight shrinkage of p is observed, which likely results because the short distance between the microrods and the plasmonic grating introduces strain in the substrates during the cure and release of the PDMS (FIG. 1A). To quantify the strain amplification, one can apply an $\varepsilon_{ex}$ of 11.8%. p increases to p' of 569±20 nm, 579±16 nm, 586±15 nm, and 799±46 nm, respectively, as G decreases (FIGS. 2b, 2d, 2f, 2h).

$$\varepsilon_{spacing} = \frac{p' - p}{p - w} \times 100\%$$

is calculated and the amplification of the local strain on the plasmonic grating is defined as $$A_{strain} = \frac{\varepsilon_{spacing}}{\varepsilon_{ex}}.$$

$A_{strain}$ increases exponentially from 1.5 to 10.2 as G decreases (FIG. 2I), consistent with the exponentially decaying strain field (FIG. 9) and quantitatively matching FE modeling results (FIG. 10).

As p (and p') is linearly related to the wavelength of the optical resonances of the plasmonic gratings (see equations 2, 3 below), one can define the amplification of the mechano-sensitivity of the plasmonic grating as the ratio between the percent increase in pitch)

$$\left(I_{pitch} = \frac{p' - p}{p} \times 100\%\right)$$

and $\varepsilon_{ex}$ such that $$A_{sensitivity} = \frac{I_{pitch}}{\varepsilon_{ex}}.$$

$A_{sensitivity}$ for the metastructures is calculated to be 0.9, 1.1, 1.2, and 5.8 as G decreases from infinity to 16 µm (FIG. 2I and Table 1 below).

Table 1. A summary of mechanical parameters used to characterize $A_{strain}$ and $A_{sensitivity}$ for metastructures with different G and L.

| G (µm) | L (µm) | p ± Δp (nm) | p' ± Δp (nm) | $\varepsilon_{spacing}$ (%) | $I_{pitch}$ (%) | $A_{strain}$ | $A_{sensitivity}$ |
|---|---|---|---|---|---|---|---|
| +∞ | 0 | 513 ± 22 | 569 ± 20 | 18.1 | 10.9 | 1.5 | 0.9 |
| 120 | 80 | 512 ± 20 | 579 ± 16 | 21.7 | 13.1 | 1.9 | 1.1 |
| 60 | 80 | 512 ± 13 | 586 ± 15 | 23.9 | 14.5 | 2.0 | 1.2 |
| 16 | 80 | 474 ± 17 | 799 ± 46 | 119.9 | 68.6 | 10.2 | 5.8 |
| 16 | 40 | 499 ± 16 | 684 ± 21 | 62.5 | 37.1 | 5.3 | 3.1 |
| 16 | 120 | 454 ± 16 | 926 ± 52 | 188.0 | 104.0 | 15.9 | 8.8 |

Since $A_{sensitivity}$ results from the amplified strain field on the plasmonic gratings, it varies exponentially with G, similar to that of $A_{strain}$. As G→+∞, $A_{sensitivity}$ is approximately 1, which reproduces the mechano-sensitivity of the previously reported stretchable metasurfaces on unstructured elastomeric substrates.[22-33]

One can further characterize the strain amplification for metastructures of different L. L is tailored from 0 µm to 40 µm, 80 µm, and 120 µm while keeping G fixed at 16 µm (FIG. 3). All other dimensions are approximately the same as those in FIG. 1C. The grating pitch p±Δp for the unstrained metastructures is 513±22 nm, 499±16 nm, 474±17 nm, 454±16 nm, respectively, as L increases (FIGS. 3A, 3C, 3E, 3G).

The decrease in p is again likely due to strain introduced during fabrication. When $\varepsilon_{ex}$=11.8% is applied, p is enlarged to 569±20 nm, 684±21 nm, 799±46 nm, and 926±52 nm, respectively (FIGS. 3B, 3D, 3F, 3H). $\varepsilon_{spacing}$ and $I_{pitch}$ are calculated accordingly, which gives $A_{strain}$ of 1.5, 5.3, 10.2, 15.9 and $A_{sensitivity}$ of 0.9, 3.1, 5.8, and 8.8 (FIG. 3I and Table 1). Both $A_{strain}$ and $A_{sensitivity}$ increase linearly with the increase in L over the investigated range (fitting in FIG. 3I), consistent with the FE modeling results (FIG. 10).

Combining the G and L dependent studies of the mechano-sensitivity of the metastructures, one can establish design rules for the microrod geometry:

$$A_{sensitivity} = 0.20 * L \times \exp\left(\frac{-G}{14.03}\right) + 0.92 \qquad (1)$$

The highest $A_{sensitivity}$ one can achieve is 8.8, for microrods with G=16 µm and L=120 which is approximately a factor of 10 greater than that of the plasmonic grating without the microrod pairs ($A_{sensitivity}$=0.9). The Au nanolines show little plastic deformation in loading and unloading of $\varepsilon_{ex}$=11.8% (FIG. 11).

Continuous Loading and Unloading of $\varepsilon_{ex}$

The variation of p when $\varepsilon_{ex}$ is continuously loaded and unloaded was investigated (FIG. 4A and FIG. 12). $\varepsilon_{ex}$ is varied 0% to 9.1% and then back to 0% in steps of approximately 1.3% for the microrod designs of G=16 µm and L=120 µm and 40 µm (FIG. 3C, 3G). $I_{pitch}$ is plotted as a function of $\varepsilon_{ex}$ in FIG. 4B. For both microrod designs, the increase (decrease) of the grating pitch shows little hysteresis and varies approximately linearly with the change of $\varepsilon_{ex}$ with slopes of $A_{sensitivity}$ of 8.3±0.3 (8.2±0.2) for L=120 µm and 3.2±0.1 (3.2±0.1) for L=40 µm, respectively (fitting in FIG. 13A). FE models (dashed lines, FIG. 4B) confirm that $I_{pitch}$ varies linearly with $\varepsilon_{ex}$, with slopes of 5.8 and 2.7 for L=120 µm and 40 µm. The modeled slopes are smaller than the experimental ones, which may be accounted for by experimental surface buckling of PDMS substrates that is not captured in the FE modeling. A cross-sectional image of the metastructure in FE modeling at $\varepsilon_{ex}$=11.8% is shown in FIG. 14. The linearity in the slopes of $I_{pitch}$ suggests that $A_{sensitivity}$ is approximately independent on $\varepsilon_{ex}$. $A_{sensitivity}$ is 8.2±1.2 and 3.6±0.5 for the metastructure design of L=120 μm and L=40 μm, respectively (FIG. 13B). For $\varepsilon_{ex}$>3%, $A_{sensitivity}$ is approximately a constant. One can hypothesize that variations in $A_{sensitivity}$ at $\varepsilon_{ex}$<3% arises from the standard deviations in $I_{pitch}$ and $\varepsilon_{ex}$ which influence the value of $A_{sensitivity}$ significantly as $\varepsilon_{ex}$ approaches 0%.

One can analyze the uniformity of the grating pitch at various $\varepsilon_{ex}$. For the microrods with L=120 μm and G=16 μm, p+Δp at $\varepsilon_{ex}$=0% is 443±24 nm, where Δp should arise solely from the fabrication tolerance (FIG. 4C). Δp remains at approximately 25 nm until $\varepsilon_{ex}$ increases above 3.9%, where Δp continuously rises to 33 nm for $\varepsilon_{ex}$=6.5% and reaches 52 nm for $\varepsilon_{ex}$=11.8%. To explain the gradually enlarged Δp, one can plot the spacing between neighboring Au nanolines as a function of the sequence of the Au nanolines in the plasmonic grating counting from top to bottom at $\varepsilon_{ex}$=0%, 6.5% and 11.8%, respectively (inset in FIG. 4C). At $\varepsilon_{ex}$=0%, the spacing varies randomly with the sequence of the Au nanolines, confirming the hypothesis that Δp represents the fabrication tolerance. At $\varepsilon_{ex}$=6.5% and 11.8%, the spacing is larger for the Au nanolines located at the top and bottom regions of the grating (FIG. 15), which is consistent with the exponentially attenuating $\varepsilon_{spacing}$ in FE models (FIG. 9). To decrease the non-uniformity in p for $\varepsilon_{ex}$>3.9%, one possible route is to develop more advanced microstructure designs. Another possible route is to develop an elastomeric substrate with a graded modulus that compensates the non-uniform distribution of $\varepsilon_{spacing}$.

The microrod design with L=120 μm and G=16 μm, which possesses the highest $A_{sensitivity}$, is cyclically stretched 10 times between $\varepsilon_{ex}$=0% and 9.1% (FIG. 4D). p and p' and their standard deviation in cycling are 451±3 nm at $\varepsilon_{ex}$ 0% and 783±19 nm at $\varepsilon_{ex}$=9.1%, which confirms the mechanical repeatability of the results.

Surface Lattice Resonance with Ultrahigh Mechano-Sensitivity

One can analyze the strain-dependent optical responses of the plasmonic lattice gratings on PDMS substrates by FDTD simulations. The light incident on the grating is linearly polarized along the y-direction (FIG. 5A). The plasmonic grating has the same dimensions as the experimentally fabricated structure shown in FIG. 1C exceptthat p is selected to vary between 300 nm to 1100 nm. Rayleigh anomalies, which are caused by the superposition of the diffractive orders propagating parallel to the substrate surface and the LSPR from the individual Au nanolines, are observed in the reflectance spectra that are plotted in a dispersion diagram as a function of p with scaled colors representing the reflectance (FIG. 5B). In the case of a one-dimensional grating, for light incident at angle θ, the wavelength (4) of the diffractive orders propagating in the substrate and in the air that travel parallel to the substrate surface are:[40]

$$\pm p_{air} p \sin(\theta) + n_{sub} p = m \cdot \lambda_D \quad (2)$$

$$+n_{pair} p \sin(\theta) + p_{air} p = m \cdot \lambda_D \quad (3)$$

where $n_{air}$ and $n_{sub}$ are the refractive indices of air and the PDMS substrate and m represents the diffractive order. The transverse LSPR of an individual Au nanoline is calculated to be at 693 nm (FIG. 16). The first- and second-order substrate modes and the first-order air mode of $\lambda_D$ are plotted in FIG. 5B (white dashed lines), which when they intersect the LSPR of the individual Au nanoline (red dashed line) result in hybridized, sharp resonance modes. As an example, the surface lattice resonance originating from the hybridization between the first-order substrate mode of $\lambda_D$ and the LSPR are presented in FIG. 5C. As p varies from 470 nm to 670 nm, corresponding to $\varepsilon_{ex}$ varying from 0.3% to 6.4% (FIG. 13), the resonance in "Sub 1" shifts from 725 nm to 1005 nm, capturing the strain-dependent optical response of the metastructures.

One can choose the metastructure that gives the highest $A_{sensitivity}$ (FIG. 3G) to experimentally demonstrate the ultrasensitive, dynamically-tunable surface lattice resonances of the plasmonic grating. In experiment, one can vary $\varepsilon_{ex}$ from 1.6% to 2.0%, 2.5%, 2.9% and 3.5%. p' is measured to be 487±22 nm, 496±22 nm, 508±24 nm, 527±21 nm, 540±16 nm, respectively (FIG. 6A and FIG. 17). The angle-resolved reflectance spectra of the plasmonic grating at various $\varepsilon_{ex}$ are collected and plotted in dispersion diagrams with the color scale representing the reflectance (FIG. 6B-6F). The calculated first-order substrate mode and the first-order air mode of $\lambda_D$ (black and red dashed lines in FIG. 6B-6F) at various $\varepsilon_{ex}$ match that found in the reflectance spectra. As p' is enlarged by $\varepsilon_{ex}$, the first-order substrate mode and the first-order air mode of $\lambda_D$ at different incident angles shift toward longer wavelengths. There is stronger reflectance in the area below the crossing point of the first-order substrate modes, suggesting that the surface lattice resonance peak profile is asymmetric, which is commonly observed in hybridized resonances.[44-46] The FDTD method is used to simulate the dispersion diagrams of the reflectance from the plasmonic grating at various $\varepsilon_{ex}$ based on the experimental grating dimensions. Experiment and simulation (FIG. 6G-6K) show excellent agreement in the wavelength shift of the diffractive orders and in the reflectance profiles.

One can extract the experimental and simulated reflectance spectra of the plasmonic grating at θ=0° from FIG. 6B-6F and FIG. 6G-6K, respectively (FIG. 6L, 6M). The resonance wavelengths are plotted as a function of $\varepsilon_{ex}$ (FIG. 6N). The surface lattice resonance varies approximately linearly from 744 nm to 836 nm as $\varepsilon_{ex}$ increases from 1.6% to 3.5% (black dots, FIG. 6N). The linear relationship between the resonance and $\varepsilon_{ex}$ is attributed to that between the $\lambda_D$ and p (eqs 2, 3) and that between p and $\varepsilon_{ex}$ (FIG. 4B). The fitting of the experimental resonance wavelengths yields a mechano-sensitivity of the plasmonic grating of 48±5 nm shift per 1% $\varepsilon_{ex}$, which is much larger than that (~5 nm/1% external strain variation) of state-of-the-art stretchable plasmonic resonators.[22,23,26] The experimental data matches that of FDTD simulations (39±3 nm/1% $\varepsilon_{ex}$) (FIG. 6N). Compared with the uniform resonance amplitude in FDTD simulations (FIG. 6M), there is a standard deviation in the amplitude (±7.2%) and a larger linewidth of the experimental resonances, which one can hypothesize are due to system variations in the data collection and variations in the dimensions of experimentally fabricated metastructures not captured in simulation (see Supporting Information). The wavelength of the surface lattice resonance of the plasmonic grating for a wider range of $\varepsilon_{ex}$ (0%-9%) is shown via FDTD simulations in FIG. 18, which could not be measured experimentally as the resonances exceeded the operating wavelength of the spectrometer camera.

Exemplary Disclosure

The following disclosure related to illustrative embodiments is exemplary only,

Materials

Copper pellets (Cr, 99.99%) are purchased from Kurt J. Lesker. Gold pellets (Au 99.9999%) are purchased from APMEX. Copper etchant is purchased from Transene company, Inc. (APS-100). Poly(methyl methacrylate) (PMMA) 495 A4, PMMA 950 A2, anisole (99%), methyl isobutyl ketone (MIBK), and Remover PG are purchased from MicroChem. Acetone (99.8%) and isopropanol (IPA) (99.5%) are purchased from Fisher Scientific. PDMS base and curing agent are purchased from Ellsworth.

Design of the Microrod Pairs on PDMS

To ensure that the Au nanolines in the plasmonic grating are not deformed by edge effects under the load $\varepsilon_{ex}$, one can design the microrod geometry as $$\frac{W}{l} = 2.$$

If the width of microrods is decreased, for example $$\frac{W}{l} = 1,$$

the Au nanolines bend into arc-shape structures due to the non-uniform $\varepsilon_{loc}$ in the gap between the pair of microrods (FIG. 7A, 7B). Such deformation would increase the complexity in analyzing the optical response of the plasmonic grating and may cause permanent plastic deformation in the Au nanolines.

Fabrication of Plasmonic Gratings and Microrods on PDMS

A 10 cm×2 cm Si wafer is cleaned by acetone and IPA using sonication for 5 min for each solution. 80 nm copper is deposited onto the Si wafer by thermal evaporation at a rate of 0.2 Å/s for the first 10 nm and then at the rate of 0.8 Å/s for the remainder. Electron-beam lithography resist PMMA 495 A4 is deposited by spin-coating at 3000 rpm for 1 min, pre-baked at 180° C. for 2 min, and allowed to cool to room temperature for 2 min. A second resist layer of PMMA 950 A2 is deposited following the same procedure. The total resist thickness is about 240 nm. The grating and the microrod patterns are exposed in an Elionix electron-beam writer operating at a 50 kV accelerating voltage and a 50 pA beam current. After exposure, the sample is developed in a 1:3 solution of MIBK and IPA for 90 s. Residual resist is removed by descuming in an $O_2$ plasma (75 mTorr, 25 W) for 25 s. A 80 nm Au layer is deposited onto the sample by thermal evaporation at 0.3 Å/s for the first 10 nm and then 0.5 Å/s for the remainder, followed by soaking in remover PG at 120° C. for 1 h to complete the lift-off process. The PDMS base is mixed at a 30 to 1 ratio with the curing agent and poured onto the patterned Si wafer to form a 1 mm thick PDMS layer. The sample is put in the vacuum oven for 30 min for degassing and then placed on a hotplate at 60 C.° for 20 h to cure. Last, the sample coated with the PDMS layer is soaked in Cu etchant (Sigma-Aldrich) for 30 h to remove the Cu film and release the PDMS layer with the pattern embedded in its surface. After the release of PDMS, it was found that shorter distances between the microrods and the plasmonic grating result in smaller p than the design value, probably because of strain induced in the substrate during the cure and release of PDMS.

AFM Measurement

AFM measurements are performed using an MFP-3D-BIO microscope (Asylum Research Corp.) with an AC240TS silicon cantilever (Olympus).

Applying $\varepsilon_{ex}$ on PDMS

A home-built mechanical stretching platform is used to apply $\varepsilon_{ex}$ on the PDMS substrate (FIG. 19). The two ends of the PDMS substrate are fixed on the stage by two clamps. A fine-pitch threaded screw is used to apply the tensile strain on the PDMS in small steps (~0.4%). The external strain is reported in terms of engineering strain applied at the two ends of the PDMS substrate. Images of the plasmonic grating and microrods at various $\varepsilon_{ex}$ are captured through a microscope (ZEISS, Axio Imager) with either a 100×, 50× or 10+ objective depending on the magnification needed.

FE Modeling

FE modeling is performed using Abaqus® ver. 6.9. A quarter of the metastructure is modeled allowing for symmetry of the system. The microrods and plasmonic grating structures are modeled with the same dimensions as those in experiments. The PDMS is taken to be 400 μm in length, 75 μm in width and 80 μm in thickness, much larger than the sizes of the metastructures to have negligible boundary effects on the results. The model uses ~78,000 3D elements (C3D8R) with a refined mesh at the corners of and near the microrod and plamsonic grating structures. Symmetric boundary conditions are applied and a displacement is applied at the boundary to stretch the PDMS to a nominal strain of 3%. For larger $\varepsilon_{ex}$, 2 D models of a vertical cross section along the center of microrod and plasmonic grating structure are used. In the 2D simulation, the model is meshed with approximately 2,200 plane strain elements (CPE8R). The size of PDMS is 1000 μm in length and 1800 μm in thickness. Applied strains up to a nominal strain of 11.8% are simulated to match those used in experiments.

The material properties of PDMS were determined by fabricating tensile specimens using the same preparation procedures as the substrates and measuring the stress-strain response in tensile tests. The measured stress-strain response was fit with a hyperelastic Mooney-Rivlin model in Abaqus® to determine the coefficients of the strain energy density function:

$$U = C_{10}(\bar{I}_1 - 3) + C_{01}(\bar{I}_2 - 3) + \frac{1}{D_1}(J_{el} - 1)^2 \tag{4}$$

The coefficients determined via fitting the experimental data were $C_{10}=0.1202$ MPa, $C_{01}=-0.040502$ MPa, and $D_1=0.2526$ MPa$^{-1}$. In eq 4, $\bar{I}_1$ and $\bar{I}_2$ are the first and second invariant of the left Cauchy-Green tensor, and $J_{el}$ is the elastic volume strain.[55] The material properties used in the analysis for Au are $E_{Au}=79$ GPa and $v_{Au}=0.4$.

Mechanical Model

The exponential relation between the amplification factors and G in FIG. 2 is concluded based on the FE modeling result in FIG. 9 which shows that $\varepsilon_{spacing}$ decays exponentially into the neighboring area near the microrods.

FDTD Simulation

FDTD simulations are performed using Lumerical FDTD Solutions software. A two-dimensional model is set up for the optical responses of the plasmonic grating in the y-z plane with periodic boundary condition. The mesh is set as 5 nm in a 500 nm by 500 nm area with the Au nanoline in the center. $n_{air}$ is set as 1 for the medium and $n_{sub}$ is set as 1.5 for PDMS. The plasmonic grating is modeled for the same dimensions as those in experiments: l=10 w=200 nm, and t=80 nm. At different $\varepsilon_{ex}$, p is set to the corresponding experimental grating pitch. For normal incident simulations, the incident plane wave type is selected as "Bloch/periodic". For the angle-dependent incidence, the light source is selected as "BEFAST".

Angle-Resolved Reflectance Measurement

A home-built, angle-resolved reflectance measurement system (FIG. 20) is used to characterize the optical response of the plasmonic grating at various $\varepsilon_{ex}$.[39] A white light beam which is linearly polarized in the y-direction is focused in the center of the plasmonic grating by an objective (60×, NA=0.7, Nikon). The spot size of the light on the grating is ~8 μm in diameter. The reflected light from the plasmonic grating is focused at the Fourier plane (back focal plane) of the objective and another lens is used to project the back focal plane onto the spectrometer and collected by a CCD camera (Princeton Instruments). The spectra baseline is collected from a Au mirror (Thorlabs). The reflectance spectra are obtained by dividing the spectra of the plasmonic grating with the baseline. The baseline-corrected reflectance spectra are fitted with basis spline to improve the smoothness.

Design of Tapered Microrods

The design of the microrods was developed by considering their influence on the distribution of local strain ($\varepsilon_{loc}$) and the deformation of the Au nanolines upon the application of external strain ($\varepsilon_{ex}$).

For the non-tapered microrod design, $\varepsilon_{loc}$ is highly concentrated at single spots near the corners of the microrods, as shown by the FE modeling result in FIG. 7C. $\varepsilon_{loc}$ near the corners of the microrods is about 58% upon the application of $\varepsilon_{ex}$=3%. $\varepsilon_{loc}$ along the topline of the microrod is about 35% on average. For the tapered microrods, the local maximum strain is distributed along the topline of the trapezoids, which is approximately 53% (FIG. 9A). The tapered microrod design focuses strain within the gap between the pair of microrods where the grating is positioned, while the non-tapered microrod design results in high strain at the corners of the microrods, which are away from the grating. The tapered microrod design was chosen as it provides an effective concentration of strain on the grating.

Related to the strain concentration at the corners, one also finds that the non-tapered microrod design leads to a more non-uniform strain distribution along the x-direction and thus larger bending in the Au nanolines in the grating. The displacement (u_y) of the $1^{st}$, $6^{th}$, $12^{th}$ Au nanolines in the grating (counting from top to bottom) at $\varepsilon_{ex}$=3% are plotted for the tapered microrod with 10 μm topline (A=10 μm, FIG. 7D), the tapered microrod with 13 μm topline (A=13 μm, FIG. 7E), and the non-tapered microrod (A=20 μm, FIG. 7F), respectively (design parameters in FIG. 1B). For the tapered microrod with 10 μm topline, the $1^{st}$ Au nanoline is bent both concavely and convexly and therefore the deformation in Au nanoline is neutralized to certain degree. For the tapered microrod with 13 μm topline and the non-tapered microrod, the Au nanolines are bent mostly concavely. The average displacement ($\overline{u\_y}$) of each Au nanoline is indicated in the FIG. 7D-7F. Comparatively, the tapered microrod with 10 μm topline creates the smallest standard errors in $\overline{u\_y}$ of the Au nanolines. One can choose the tapered microrods with 10 μm topline to also reduce the variation in u_y and therefore the deformation in Au nanolines.

The displacement of the experimentally fabricated Au nanolines at $\varepsilon_{ex}$=11.8% is analyzed for the tapered microrods with L=40 μm, G=16 μm (FIG. 3C, FIG. 7G) and L=120 μm, G=16 μm (FIG. 3G, FIG. 7H). The Au nanolines remain flat for the microrods of L=40 μm, G=16 μm (FIG. 7G). The microrod with L=120 μm creates higher $\varepsilon_{loc}$ in the grating, which bends the Au nanolines to a small degree. The bending of the Au nanolines and the non-uniformity in $\varepsilon_{loc}$ in the y-direction could likely be further reduced with more advanced metastructure geometries, but extensive optimization studies would be required to develop such designs.

Cyclical Stretching of the Plasmonic Grating on Microstructured Elastomeric Substrate The metastructure with L=120 μm and G=16 μm is cyclically stretched 10 times between $\varepsilon_{ex}$=0% and 9.1%. There is a deviation (±19 nm) in p' at $\varepsilon_{ex}$=9.1%. One finds that the deviation is consistent with a slight buckling of the microrods in the cycling processes (shown in FIG. 21). The roughness of the Au layer on PDMS substrate and the buckling of the Au layer upon application of external strain have also been reported in previous publications.

Discussion on the Limit of the Mechano-Sensitivity

To discuss the limit of the mechano-sensitivity of the metastructure, one can consider the magnitude of the applied $\varepsilon_{ex}$ at the same time. At the same magnitude of the applied $\varepsilon_{ex}$, higher $A_{sensitivity}$ can result in higher $\varepsilon_{loc}$ around the metastructure on the PDMS substrate, which can eventually lead to plastic deformation of the metastructure/PDMS and/or delamination at the Au-PDMS interface. To give an example, for $\varepsilon_{ex}$=9.1%, one can demonstrate in experiments and simulations that $A_{sensitivity}$ can be tuned from 0.9 to 8.8 by increasing the length of the microrods (L) or decreasing the gap between the microrods (G). In Table 1, it is shown that $\varepsilon_{spacing}$ in the grating increases from 18% to 188% as $A_{sensitivity}$ increases. It is possible to further improve $A_{sensitivity}$ by further increasing L or decreasing G. However, at the same time, the $E_{loc}$ around the metastructure will also increase, and eventually cause plastic deformation in the metastructure/PDMS or delamination at the Au-PDMS interface. The limit of the mechano-sensitivity is reached when the plastic deformation in the device occurs or the metastructure delaminates from the substrate. It should be noted that for a smaller $\varepsilon_{ex}$, for example 3%, the limit of $A_{sensitivity}$ will be larger than that for $\varepsilon_{ex}$=11.8%, since the smaller $\varepsilon_{ex}$ will create a smaller $\varepsilon_{loc}$ around the metastructure on the PDMS substrate.

To improve the limit of $A_{sensitivity}$, the maximum strain that the metastructure/PDMS and the interface can withstand needs to be enhanced. Some possible ways are to fabricate microrods from other materials that have higher yield strain than Au (for example, Ni), use emerging elastomeric substrates that have higher yield strain than PDMS, and optimizing the bonding at the interface between the metasurface and the elastomer substrate.

Surface Lattice Resonances Based on Plasmonic Gratings

Surface lattice resonances arise from the hybridization of the diffractive orders propagating parallel to the substrate surface and the transverse LSPR from the individual Au nanolines in the plasmonic grating. The wavelength of the surface lattice resonance is determined by both p and the incident angle, as shown in equations 2 and 3. As an example, the surface lattice resonances originating from the hybridization of the first-order substrate mode of $\lambda_D$ and the transverse LSPR from the individual Au nanolines at normal incidence is calculated by FDTD simulation and plotted as a function of p in FIG. 5C. As p increases from 470 nm to 670 nm and therefore $\lambda_D$ gradually moves away from the hybridization regime (FIG. 5B), the full width at half maximum (fwhm) of the resonance remains narrow at 72±31 nm due to diffraction. The resonance amplitude decreases from 85% to 30% because of progressively weaker coupling between the diffraction mode and the transverse LSPR of the individual Au nanolines.

Scattering Efficiency of the Plasmonic Grating

Figure 22L:
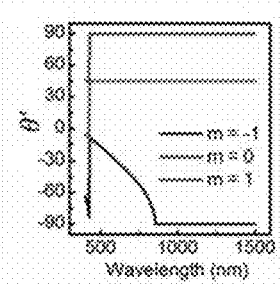
Figure 22M:
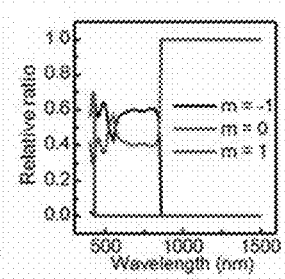

One can investigate the scattering of the plasmonic grating. The scattered light from the plasmonic grating is dominated by the diffractive orders. One can calculate the $0^{th}$ order and $1^{st}$ order of diffraction (m=0, ±1) from the grating (w=200 nm, p=500 nm, t=80 nm) by FDTD simulation to illustrate the scattering efficiency (FIG. 22). Diffractive orders higher than 1 are not considered here as they are not supported by the grating in the wavelength range investigated. One can calculate the relative ratio of the intensity of the 0th order and $1^{st}$ order diffraction, with the incident angle (0) varying between 0° and 45° and the incident wavelength varying between 400 nm and 1500 nm. The scattering efficiency of the grating (or the percentage of the $1^{st}$ order diffraction in the diffracted light) depends on both 0 and the incident wavelength, as shown in FIG. 22D, 22G, 22J, 22M. As 0 increases, a wider range of wavelengths is scattered in the $1^{st}$ order diffraction. Most light is scattered at θ=45°, where the scattered light wavelength ranges from 400 nm to 850 nm and the angle (0') varies between −9° and −90° (FIG. 22L). The scattering efficiency (shown as relative ratio) approximately varies between 0 and 0.7 (FIG. 22M) at different wavelengths.

Angle-Resolved Reflectance Spectra

In the angle-resolved reflectance spectra, there is a standard deviation in the amplitude of the resonances (±7.2%). The standard deviation may arise from the slight variation in the light source profile over the measurement time. Another possibility is that there is a standard deviation in the spot size of the focused incident light on the plasmonic grating during the measurements at various $\varepsilon_{ex}$. Variation in spot size could result in a difference in reflectance in the angle-resolved reflectance spectra.

Linear Fits of the Reflectance Peak Positions as a Function of $\varepsilon_{ex}$ In the angle-resolved reflectance measurements, one can obtain the wavelength of the surface lattice resonances at normal incidence (FIG. 6N) at various $\varepsilon_{ex}$. Linear fitting is used to fit the experimental resonance=47.7×$\varepsilon_{ex}$×100+675.6 (black dashes) and simulated resonance=38.9×$\varepsilon_{ex}$×100+ 678.1 (red dashes) with r-square at or above 0.96.

EXEMPLARY EMBODIMENTS

The following embodiments are exemplary only and do not serve to limit the scope of the present disclosure or the appended claims.

Embodiment 1. A mechanically responsive component, comprising: an elastic substrate, a first elongate microbody disposed on the elastic substrate, the first elongate microbody defining a major axis, a proximal end, and a distal end, the first elongate microbody defining a maximum width measured perpendicular to the major axis, and the width of the first elongate microbody measured at the proximal end being less than the maximum width, a second elongate microbody disposed on the elastic substrate, the second elongate microbody defining a major axis, a proximal end, and a distal end, the proximal end of the first elongate microbody being disposed opposite the proximal end of the second elongate microbody so as to define a gap between the proximal end of the first elongate microbody and the proximal end of the second elongate microbody; and a strain-sensitive structure disposed on the elastic substrate, the strain-sensitive structure being disposed in the gap between the proximal end of the first elongate microbody and the proximal end of the second elongate microbody, and the component being configured so as locally amplify, at the location of the strain-sensitive structure, an external strain applied to the elastic substrate.

The first and second elongate microbodies can be symmetric, and can even be identical to one another.

Embodiment 2. The mechanically responsive component of Embodiment 1, wherein the proximal end of the first elongate microbody and the proximal end of the second elongate microbody are separated by less than about 120 micrometers. The separation between the proximal ends of the first and second microbodies can be in the range of from about 1 micrometer to about 1000 micrometers, or from about 10 micrometers to about 500 micrometers, or even from about 15 micrometers to about 250 micrometers, e.g., about 20 to about 220 micrometers, about 35 to about 210 micrometers, about 50 to about 180 micrometers, about 70 to about 160 micrometers, about 90 to about 150 micrometers, or even from about 110 to about 130 micrometers.

Embodiment 3. The mechanically responsive component of Embodiment 2, wherein the proximal end of the first elongate microbody and the proximal end of the second elongate microbody are separated by from about 16 to about 120 micrometers, e.g., from about 16 to about 120 micrometers, from about 20 to about 110 micrometers, from about 30 to about 100 micrometers, from about 45 to about 85 micrometers, or from about 55 to about 70 micrometers.

Embodiment 4. The mechanically responsive component of any one of Embodiments 1-3, wherein the distal end of the first elongate microbody defines a width greater than a width of the proximal end of the first elongate microbody. As an example, a microbody can taper, in width, from its distal end down to its proximal end. The taper can be constant in nature, but this is not a requirement.

Embodiment 5. The mechanically responsive component of any one of Embodiments 1-4, wherein the distal end of the second elongate microbody defines a width greater than a width of the proximal end of the second elongate microbody.

Embodiment 6. The mechanically responsive component of any of Embodiments 1-5, wherein the first elongate microbody defines a variable width along the major axis of the first elongate microbody.

Embodiment 7. The mechanically responsive component of any one of Embodiments 1-6, wherein the second elongate microbody defines a variable width along the major axis of the second elongate microbody.

Embodiment 8. The mechanically responsive component of any one of Embodiments 1-7, wherein (a) the first elongate microbody comprises two edges converging toward the proximal end of the first elongate microbody, (b) the second elongate microbody comprises two edges converging toward the proximal end of the second elongate microbody, or both (a) and (b).

Embodiment 9. The mechanically responsive component of any one of Embodiments 1-8, wherein the strain-sensitive structure comprises a plurality of first bodies aligned substantially parallel along a first direction, the plurality of first bodies optionally being arranged at a regular pitch, and the first direction optionally being essentially perpendicular to at least one of the major axis of the first elongate microbody and the major axis of the second elongate microbody.

In one example embodiment, the pitch between first bodies (when no strain is applied) can be in the range of, e.g., from about 10 nm to about 5 micrometers, e.g., 500 nm, or from about 50 nm to about 4 micrometers, from about 100 nm to about 3 micrometers, or even from about 500 nm to about 1 mictometer. (1) In the component design without applying any external strain, the likely min/max range of the pitch between bodies is: about tens of nanometers (e.g. 50 nm) to several micrometers (e.g., 5 micrometers), as long as it can fit within the gap between the first and second microbodies. Under the application of external strain, the spacing between such bodies can vary, e.g., from about 450 nm to about 930 nm.

Embodiment 10. The mechanically responsive component of Embodiment 9, wherein a first body defines a cross-sectional dimension measured in the first direction of from about 0.01 to about 10 micrometers.

Embodiment 11. The mechanically responsive component of any one of Embodiments 9-10, wherein a first body defines a cross-sectional dimension, measured perpendicular to the first direction, of from about 0.01 to about 10 micrometers, e.g., about 0.2 micrometers, or from about 0.01 to about 10 micrometers, from about 0.05 to about 9 micrometers, from about 0.1 to about 7 micrometers, from about 0.3 to about 6 micrometers, from about 0.7 to about 4 micrometers, or from about 0.9 to about 2 micrometers.

Embodiment 12. The mechanically responsive component of any one of Embodiments 9-11, wherein the strain-sensitive structure comprises a plurality of second bodies aligned substantially parallel along a second direction.

Embodiment 13. The mechanically responsive component of Embodiment 12, wherein a second body defines a cross-sectional dimension, measured in the second direction, of from about 0.01 to about 10 micrometers, e.g., about 0.2 micrometers, or from about 0.01 to about 10 micrometers, from about 0.05 to about 9 micrometers, from about 0.1 to about 7 micrometers, from about 0.3 to about 6 micrometers, from about 0.7 to about 4 micrometers, or from about 0.9 to about 2 micrometers. The ranges of the length and width of the second body are the same as the first body.

Embodiment 15. The mechanically responsive component of any one of Embodiments 12-13, wherein a second body defines a cross-sectional dimension, measured perpendicular to the second direction, of from about 0.01 to about 1 micrometer, e.g., from about 0.1 to about 1 micrometer, from about 0.3 to about 0.9 micrometers, or from about 0.4 to about 0.6 micrometers.

Embodiment 15. The mechanically responsive component of any one of Embodiments 12-14, wherein the second direction is angularly offset from the first direction.

Embodiment 16. The mechanically responsive component of Embodiment 15, wherein the second direction is essentially perpendicular to the first direction.

Embodiment 17. The mechanically responsive component of any one of Embodiments 1-16, wherein the strain-sensitive structure comprises a plurality of circular bodies.

Embodiment 18. The mechanically responsive component of any one of Embodiments 1-17, wherein the strain-sensitive structure is characterized as a plasmonic grating, a Bragg grating, an arbitrary array of plasmonic structures, an assembly of photonic crystals, a capacitor, a resistor, a crack junction, a piezoelectric material, or any combination thereof.

Embodiment 19. The mechanically responsive component of any one of Embodiments 1-18, wherein the mechanically responsive component is configured so to exhibit a strain amplification (defined as $$A_{strain} = \frac{\varepsilon_{spacing}}{\varepsilon_{ex}}\Big)$$

of from about 1 to about 20. Stain amplification can be, e.g., from about 1.5 to 15.9, from about 1.7 to about 13.8, from about 2.2 to about 12.7, from about 3.7 to about 11.2, from about 4.4 to about 9.8, from about 5.5 to about 8.1, or from about 6.1 to about 7.2.

Embodiment 20. The mechanically responsive component of any one of Embodiments 1-18, wherein the mechanically responsive component is configured so to exhibit a strain sensitivity (defined as $$A_{sensitivity} = \frac{I_{pitch}}{\varepsilon_{ex}}\Big)$$

of from about 1 to about 9.0, e.g., from about 1 to about 9, from about 1.3 to about 7.7, from about 1.8 to about 7, from about 2.2 to about 6.8, from about 2.6 to about 6.3, from about 2.9 to about 5.7, or even from about 3.4 to about 4.4.

Embodiment 21. A device, the device comprising a component according to any one of Embodiments 1-20.

Embodiment 22. The device of Embodiment 21, wherein the device is characterized as a strain sensor, a strain gauge, an optical sensor, a wearable sensor, a skin-mountable sensor, a flexible electronic component, or any combination thereof.

Embodiment 23. A method, comprising: exerting a strain on a component according to any one of Embodiments 1-20, wherein the strain-sensitive structure converts the strain to a signal (a resistance, a capacitance, a reflectance, a transmission, or other signal) and/or a change in signal. One can monitor a signal (e.g., a transmission, a reflectance) associated with the component before, during, and/or after application of the strain.

Embodiment 24. The method of Embodiment 23, further comprising correlating the signal to the strain.

Embodiment 25. The method of Embodiment 23, further comprising modulating the strain at least partially in response to the signal. For example, one can increase or decrease the strain at least partially in response to the signal. In this way, one can adjust the optical or other properties of the component; in this way, a user can utilize the component as an adjustable grating, a filter, an antenna, and the like. By modulating the strain experienced by the component, one can adjust the properties of the component in essentially real-time, thereby allowing one to use a single component for a variety of applications. Strain can also be adjusted so as to physically relax (or tighten) the component, e.g., in applications where the component is being used to physically interact with a user or other object.

Embodiment 26. A method, comprising: exerting a strain on a component according to any one of Embodiments 1-20 so as to effect a change in an optical property of the strain-sensitive structure.

Embodiment 27. A method, comprising: exerting a strain on a component according to any one of Embodiments 1-20 so as to effect a change in an electrical property of the strain-sensitive structure.

REFERENCES

The following references are provided for convenience.

Smith, D. R., Pendry, J. B., Wilshire, M. C. K., Metamaterials and Negative Refractive Index. *Science* 2004, 305, 788-792.

Shalaev, V. M. Optical Negative-Index Metamaterials. *Nat. Photonics* 2007, 1, 41-48.

Liberal, I.; Engheta, N. Near-Zero Refractive Index Photonics. *Nat. Photonics* 2017, 11, 149-158.

Khorasaninejad, M.; Capasso, F. Metalenses: Versatile Multifunctional Photonic Components. *Science* 2017, 358, 1146.

Falcone, F.; Lopetegi, T.; Laso, M. A. G.; Baena, J. D.; Bonache, J.; Beruete, M.; Marqués, R.; Martin, F.; Sorolla, M. Babinet Principle Applied to the Design of Metasurfaces and Metamaterials. *Phys. Rev. Lett.* 2004, 93, 197401.

Zhao, Y.; Belkin, M. a.; Alù, A. Twisted Optical Metamaterials for Planarized Ultrathin Broadband Circular Polarizers. *Nat. Commun.* 2012, 3, 870.

Ellenbogen, T.; Seo, K.; Crozier, K. B. Chromatic Plasmonic Polarizers for Active Visible Color Filtering and Polarimetry. *Nano Lett.* 2012, 12, 1026-1031.

Chen, W.; Tymchenko, M.; Gopalan, P.; Ye, X.; Wu, Y.; Zhang, M.; Murray, C. B.; Alu, A.; Kagan, C. R. Large-Area Nanoimprinted Colloidal Au Nanocrystal-Based Nanoantennas for Ultrathin Polarizing Plasmonic Metasurfaces. *Nano Lett.* 2015, 15, 5254-5260.

Aieta, F.; Genevet, P.; Kats, M. a; Yu, N.; Blanchard, R.; Gaburro, Z.; Capasso, F. Aberration-Free Ultrathin Flat Lenses and Axicons at Telecom Wavelengths Based on Plasmonic Metasurfaces. *Nano Lett.* 2012, 12, 4932-4936.

Khorasaninejad, M.; Aieta, F.; Kanhaiya, P.; Kats, M. A.; Genevet, P.; Rousso, D.; Capasso, F. Achromatic Metasurface Lens at Telecommunication Wavelengths. *Nano Lett.* 2015, 15, 5358-5362.

Ni, X.; Kildishev, A. V.; Shalaev, V. M. Metasurface Holograms for Visible Light. *Nat. Commun.* 2013, 4, 2807.

Zheng, G.; Mühlenbernd, H.; Kenney, M.; Li, G.; Zentgraf, T.; Zhang, S. Metasurface Holograms Reaching 80% Efficiency. *Nat. Nanotechnol.* 2015, 10, 308-312.

Yu, N.; Capasso, F. Flat Optics with Designer Metasurfaces. *Nat. Mater.* 2014, 13, 139-150.

Zheludev, N. I.; Kivshar, Y. S. From Metamaterials to Metadevices. *Nat. Mater.* 2012, 11, 917-924.

Zheludev, N. I.; Plum, E. Reconfigurable Nanomechanical Photonic Metamaterials. *Nat. Nanotechnol.* 2016, 11, 16-22.

Lapine, M.; Powell, D.; Gorkunov, M.; Shadrivov, I.; Marqús, R.; Kivshar, Y. Structural Tunability in Metamaterials. *Appl. Phys. Lett.* 2009, 95, 084105.

Tao, H.; Strikwerda, A. C.; Fan, K.; Padilla, W. J.; Zhang, X.; Averitt, R. D. Reconfigurable Terahertz Metamaterials. *Phys. Rev. Lett.* 2009, 103, 147401.

Chu, C. H.; Tseng, M. L.; Chen, J.; Wu, P. C.; Chen, Y.-H.; Wang, H.-C.; Chen, T.-Y.; Hsieh, W. T.; Wu, H. J.; Sun, G.; Tsai, D. P. Active Dielectric Metasurface Based on Phase-Change Medium. *Laser Photon. Rev.* 2016, 10, 986-994.

Ou, J.-Y.; Plum, E.; Zhang, J.; Zheludev, N. I. An Electromechanically Reconfigurable Plasmonic Metamaterial Operating in the near-Infrared. *Nat. Nanotechnol.* 2013, 8, 252-255.

Arbabi, E.; Arbabi, A.; Kamali, S. M.; Horie, Y.; Faraji-Dana, R.; Faraon, A. MEMS-Tunable Dielectric Metasurface Lens. *Nat. Commun.* 2018, 9, 812.

Huang, Y.-W.; Lee, H. W. H.; Sokhoyan, R.; Pala, R. A.; Thyagarajan, K.; Han, S.; Tsai, D. P.; Atwater, H. A. Gate-Tunable Conducting Oxide Metasurfaces. *Nano Lett.* 2016, 16, 5319-5325.

Pryce, I. M.; Aydin, K.; Kelaita, Y. A.; Briggs, R. M.; Atwater, H. A. Highly Strained Compliant Optical Metamaterials with Large Frequency Tunability. *Nano Lett.* 2010, 10, 4222-4227.

Gao, L.; Zhang, Y.; Zhang, H.; Doshay, S.; Xie, X.; Luo, H.; Shah, D.; Shi, Y.; Xu, S.; Fang, H.; Fan, J. A.; Nordlander, P.; Huang, Y.; Rogers, J. A. Optics and Nonlinear Buckling Mechanics in Large-Area, Highly Stretchable Arrays of Plasmonic Nanostructures. *ACS Nano* 2015, 9, 5968-5975.

Yoo, D.; Johnson, T. W.; Cherukulappurath, S.; Norris, D. J.; Oh, S.-H. Template-Stripped Tunable Plasmonic Devices on Stretchable and Rollable Substrates. *ACS Nano* 2015, 9, 10647-10654.

Aksu, S.; Huang, M.; Artar, A.; Yanik, A. A.; Selvarasah, S.; Dokmeci, M. R.; Altug, H. Flexible Plasmonics on Unconventional and Nonplanar Substrates. *Adv. Mater.* 2011, 23, 4422-4430.

Yang, A.; Hryn, A. J.; Bourgeois, M. R.; Lee, W.-K.; Hu, J.; Schatz, G. C.; Odom, T. W. Programmable and Reversible Plasmon Mode Engineering. *Proc. Natl. Acad. Sci.* 2016, 113, 14201-14206.

Zhou, W.; Odom, T. W. Tunable Subradiant Lattice Plasmons by out-of-Plane Dipolar Interactions. *Nat. Nanotechnol.* 2011, 6, 423-427.

Gutruf, P.; Zou, C.; Withayachumnankul, W.; Bhaskaran, M.; Sriram, S.; Fumeaux, C. Mechanically Tunable Dielectric Resonator Metasurfaces at Visible Frequencies. *ACS Nano* 2016, 10, 133-141.

Liu, X.; Huang, Z.; Zhu, C.; Wang, L.; Zang, J. Out-of-Plane Designed Soft Metasurface for Tunable Surface Plasmon Polariton. *Nano Lett.* 2018, 18, 1435-1441.

Tseng, M. L.; Yang, J.; Semmlinger, M.; Zhang, C.; Nordlander, P.; Halas, N. J. Two-Dimensional Active Tuning of an Aluminum Plasmonic Array for Full-Spectrum Response. *Nano Lett.* 2017, 17, 6034-6039.

Kristensen, A.; Yang, J. K. W.; Bozhevolnyi, S. I.; Link, S.; Nordlander, P.; Halas, N. J.; Mortensen, N. A. Plasmonic Colour Generation. *Nat. Rev. Mater.* 2016, 2, 16088.

Kumar, K.; Duan, H.; Hegde, R. S.; Koh, S. C. W.; Wei, J. N.; Yang, J. K. W. Printing Colour at the Optical Diffraction Limit. *Nat. Nanotechnol.* 2012, 7, 557-561.

Ee, H. S.; Agarwal, R. Tunable Metasurface and Flat Optical Zoom Lens on a Stretchable Substrate. *Nano Lett.* 2016, 16, 2818-2823.

Kamali, S. M.; Arbabi, E.; Arbabi, A.; Horie, Y.; Faraon, A. Highly Tunable Elastic Dielectric Metasurface Lenses. *Laser Photon. Rev.* 2016, 10, 1002-1008.

Malek, S. C.; Ee, H.; Agarwal, R. Strain Multiplexed Metasurface Holograms on a Stretchable Substrate. *Nano Lett.* 2017, 17, 3641-3645.

She, A.; Zhang, S.; Shian, S.; Clarke, D. R.; Capasso, F. Adaptive Metalenses with Simultaneous Electrical Control of Focal Length, Astigmatism, and Shift. *Sci. Adv.* 2018, 4, eaap9957.

Polavarapu, L.; Liz-Marzán, L. M. Towards Low-Cost Flexible Substrates for Nanoplasmonic Sensing. *Phys. Chem. Chem. Phys.* 2013, 15, 5288.

Yang, A.; Hryn, A. J.; Bourgeois, M. R.; Lee, W.-K.; Hu, J.; Schatz, G. C.; Odom, T. W. Programmable and Reversible Plasmon Mode Engineering. *Proc. Natl. Acad. Sci.* 2016, 113, 14201-14206.

Liu, W.; Lee, B.; Naylor, C. H.; Ee, H.-S.; Park, J.; Johnson, A. T. C.; Agarwal, R. Strong Exciton-Plasmon Coupling in MoS2 Coupled with Plasmonic Lattice. *Nano Lett.* 2016, 16, 1262-1269.

Kravets, V. G.; Schedin, F.; Grigorenko, A. N. Extremely Narrow Plasmon Resonances Based on Diffraction Coupling of Localized Plasmons in Arrays of Metallic Nanoparticles. *Phys. Rev. Lett.* 2008, 101, 087403.

Hu, S. M. Film-edge-induced Stress in Substrates. *J. Appl. Phys.* 1979, 50, 4661-4666.

Rayleigh, Lord. On the Dynamical Theory of Gratings. *Proc. R. Soc. A* 1907, 79, 399-416.

Ye, S.; Zhang, X.; Chang, L.; Wang, T.; Li, Z.; Zhang, J.; Yang, B. High-Performance Plasmonic Sensors Based on Two-Dimensional Ag Nanowell Crystals. *Adv. Opt. Mater.* 2014, 2, 779-787.

Luk'yanchuk, B.; Zheludev, N. I.; Maier, S. A.; Halas, N. J.; Nordlander, P.; Giessen, H.; Chong, C. T. The Fano Resonance in Plasmonic Nanostructures and Metamaterials. *Nat. Mater.* 2010, 9, 707-715.

Hao, F.; Sonnefraud, Y.; Dorpe, P. Van; Maier, S. A.; Halas, N. J.; Nordlander, P. Symmetry Breaking in Plasmonic Nanocavities: Subradiant LSPR Sensing and a Tunable Fano Resonance. *Nano Lett.* 2008, 8, 3983-3988.

Greybush, N. J.; Liberal, I.; Malassis, L.; Kikkawa, J. M.; Engheta, N.; Murray, C. B.; Kagan, C. R. Plasmon Resonances in Self-Assembled Two-Dimensional Au Nanocrystal Metamolecules. *ACS Nano* 2017, 11, 2917-2927.

Li, C.-H.; Wang, C.; Keplinger, C.; Zuo, J.-L.; Jin, L.; Sun, Y.; Zheng, P.; Cao, Y.; Lissel, F.; Linder, C.; You, X.-Z.; Bao, Z. A Highly Stretchable Autonomous Self-Healing Elastomer. *Nat. Chem.* 2016, 8, 618-624.

Olson, J.; Manjavacas, A.; Liu, L.; Chang, W.-S.; Foerster, B.; King, N. S.; Knight, M. W.; Nordlander, P.; Halas, N. J.; Link, S. Vivid, Full-Color Aluminum Plasmonic Pixels. *Proc. Natl. Acad. Sci.* 2014, 111, 14348-14353.

Zhou, W.; Dridi, M.; Suh, J. Y.; Kim, C. H.; Co, D. T.; Wasielewski, M. R.; Schatz, G. C.; Odom, T. W. Lasing Action in Strongly Coupled Plasmonic Nanocavity Arrays. *Nat. Nanotechnol.* 2013, 8, 506-511.

Wang, H.; Levin, C. S.; Halas, N. J. Nanosphere Arrays with Controlled Sub-10-Nm Gaps as Surface-Enhanced Raman Spectroscopy Substrates. *J. Am. Chem. Soc.* 2005, 127, 14992-14993.

Yamada, T.; Hayamizu, Y.; Yamamoto, Y.; Yomogida, Y.; Izadi-Najafabadi, A.; Futaba, D. N.; Hata, K. A Stretchable Carbon Nanotube Strain Sensor for Human-Motion Detection. *Nat. Nanotechnol.* 2011, 6, 296-301.

Kang, D.; Pikhitsa, P. V.; Choi, Y. W.; Lee, C.; Shin, S. S.; Piao, L.; Park, B.; Suh, K.-Y.; Kim, T.; Choi, M. Ultrasensitive Mechanical Crack-Based Sensor Inspired by the Spider Sensory System. *Nature* 2014, 516, 222-226.

Amjadi, M.; Kyung, K. U.; Park, I.; Sitti, M. Stretchable, Skin-Mountable, and Wearable Strain Sensors and Their Potential Applications: A Review. *Adv. Funct. Mater.* 2016, 26, 1678-1698.

Lu, N.; Lu, C.; Yang, S.; Rogers, J. Highly Sensitive Skin-Mountable Strain Gauges Based Entirely on Elastomers. *Adv. Funct. Mater.* 2012, 22, 4044-4050.

*Abaqus Theory Manual*, v. 6.9; Dassault Systemes Simulia Corp.: Providence, 2009

Zhang, J.; Yan, Y.; Miao, P.; Cai, J. Fabrication of Gold-Coated PDMS Surfaces with Arrayed Triangular Micro/nanopyramids for Use as SERS Substrates. *Beilstein J. Nanotechnol.* 2017, 8, 2271-2282.

Lacour, S. P.; Jones, J.; Wagner, S.; Li, T.; Suo, Z. Stretchable Interconnects for Elastic Electronic Surfaces. *Proc. IEEE* 2005, 93, 1459-1467.

Rogel, R.; Borgne, B. L.; Mohammed-Brahim, T.; Jacques, E.; Harnois, M. Spontaneous Buckling of Multiaxially Flexible and Stretchable Interconnects Using PDMS/Fibrous Composite Substrates. *Adv. Mater. Interfaces* 2017, 4, 1600946.

Caglayan, H.; Hong, S.-H.; Edwards, B.; Kagan, C. R.; Engheta, N. Near-Infrared Metatronic Nanocircuits by Design. *Phys. Rev. Lett.* 2013, 111, 073904.

What is claimed:

1. A mechanically responsive component, comprising:
an elastic substrate,
a first elongate microbody disposed on the elastic substrate,
the first elongate microbody defining a major axis, a proximal end, and a distal end,
the first elongate microbody defining a maximum width measured perpendicular to the major axis, and
the width of the first elongate microbody measured at the proximal end being less than the maximum width,
a second elongate microbody disposed on the elastic substrate,
the second elongate microbody defining a major axis, a proximal end, and a distal end,
the proximal end of the first elongate microbody being disposed opposite the proximal end of the second elongate microbody so as to define a gap between the proximal end of the first elongate microbody and the proximal end of the second elongate microbody; and
a strain-sensitive structure disposed on the elastic substrate,
the strain-sensitive structure being disposed in the gap between the proximal end of the first elongate microbody and the proximal end of the second elongate microbody, and
the component being configured so as locally amplify, at the location of the strain-sensitive structure, an external strain applied to the elastic substrate.

2. The mechanically responsive component of claim 1, wherein the proximal end of the first elongate microbody and the proximal end of the second elongate microbody are separated by less than about 120 micrometers.

3. The mechanically responsive component of claim 2, wherein the proximal end of the first elongate microbody and the proximal end of the second elongate microbody are separated by from about 16 to about 120 micrometers.

4. The mechanically responsive component of claim 1, wherein the distal end of the first elongate microbody defines a width greater than a width of the proximal end of the first elongate microbody.

5. The mechanically responsive component of claim 1, wherein the distal end of the second elongate microbody defines a width greater than a width of the proximal end of the second elongate microbody.

6. The mechanically responsive component of claim 1, wherein the first elongate microbody defines a variable width along the major axis of the first elongate microbody.

7. The mechanically responsive component of claim 1, wherein the second elongate microbody defines a variable width along the major axis of the second elongate microbody.

8. The mechanically responsive component of claim 1, wherein (a) the first elongate microbody comprises two edges converging toward the proximal end of the first elongate microbody, (b) the second elongate microbody comprises two edges converging toward the proximal end of the second elongate microbody, or both (a) and (b).

9. The mechanically responsive component of claim 1, wherein the strain-sensitive structure comprises a plurality of first bodies aligned substantially parallel along a first direction,
the plurality of first bodies optionally being arranged at a regular pitch, and
the first direction optionally being essentially perpendicular to at least one of the major axis of the first elongate microbody and the major axis of the second elongate microbody.

10. The mechanically responsive component of claim 9, wherein a first body defines a cross-sectional dimension measured in the first direction of from about 0.01 to about 10 micrometers.

11. The mechanically responsive component of claim 9, wherein a first body defines a cross-sectional dimension, measured perpendicular to the first direction, of from about 0.01 to about 1 micrometers.

12. The mechanically responsive component of claim 9, wherein the strain-sensitive structure comprises a plurality of second bodies aligned substantially parallel along a second direction.

13. The mechanically responsive component of claim 12, wherein a second body defines a cross-sectional dimension, measured in the second direction, of from about 0.01 to about 10 micrometers.

14. The mechanically responsive component of claim 12, wherein a second body defines a cross-sectional dimension, measured perpendicular to the second direction, of from about 0.01 to about 1 micrometers.

15. The mechanically responsive component of claim 12, wherein the second direction is angularly offset from the first direction.

16. The mechanically responsive component of claim 15, wherein the second direction is essentially perpendicular to the first direction.

17. The mechanically responsive component of claim 1, wherein the strain-sensitive structure comprises a plurality of circular bodies.

18. The mechanically responsive component of claim 1, wherein the strain-sensitive structure is characterized as a plasmonic grating, a Bragg grating, an arbitrary array of plasmonic structures, an assembly of photonic crystals, a capacitor, a resistor, a crack junction, a piezoelectric material, or any combination thereof.

19. The mechanically responsive component of claim 1, wherein the mechanically responsive component is configured so to exhibit a strain amplification of from about 1 to about 20.

20. The mechanically responsive component of claim 1, wherein the mechanically responsive component is configured so to exhibit a strain sensitivity of from about 1 to about 9.0.

21. A device, the device comprising a component according to claim 1.

22. The device of claim 21, wherein the device is characterized as a strain sensor, a strain gauge, an optical sensor, a wearable sensor, a skin-mountable sensor, a flexible electronic component, or any combination thereof.

23. A method, comprising:
exerting a strain on a component according to claim 1, wherein the strain-sensitive structure converts the strain to a signal.

24. The method of claim 23, further comprising correlating the signal to the strain.

25. The method of claim 23, further comprising modulating the strain at least partially in response to the signal.

26. A method, comprising:
exerting a strain on a component according to claim 1 so as to effect a change in an optical property of the strain-sensitive structure.

27. A method, comprising:
exerting a strain on a component according to claim 1 so as to effect a change in an electrical property of the strain-sensitive structure.

* * * * *